United States Patent
Maina et al.

(10) Patent No.: US 7,695,964 B2
(45) Date of Patent: Apr. 13, 2010

(54) COMPOSITIONS AND METHODS FOR GENERATING SHORT DOUBLE-STRANDED RNA USING MUTATED RNASE III

(75) Inventors: Claude V. Maina, West Newbury, MA (US); George Tzertzinis, Cambridge, MA (US); Sanjay Kumar, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 271 days.

(21) Appl. No.: 10/586,720

(22) PCT Filed: Jan. 21, 2005

(86) PCT No.: PCT/US2005/002029

§ 371 (c)(1),
(2), (4) Date: Jul. 20, 2006

(87) PCT Pub. No.: WO2005/072272

PCT Pub. Date: Aug. 11, 2005

(65) Prior Publication Data

US 2007/0155684 A1    Jul. 5, 2007

Related U.S. Application Data

(60) Provisional application No. 60/538,805, filed on Jan. 23, 2004, provisional application No. 60/543,880, filed on Feb. 12, 2004, provisional application No. 60/572,240, filed on May 18, 2004.

(51) Int. Cl.
*C12N 5/00* (2006.01)
*C12N 5/02* (2006.01)
*G01N 33/53* (2006.01)

(52) U.S. Cl. .................................. 435/375; 435/7.6

(58) Field of Classification Search .................. 435/6, 435/91.1, 325, 375
See application file for complete search history.

(56) References Cited

U.S. PATENT DOCUMENTS

2004/0038278 A1    2/2004    Tzertzinis et al.

FOREIGN PATENT DOCUMENTS

| WO | WO 99/32619 | 7/1999 |
|----|----|----|
| WO | WO 01/29058 | 4/2001 |
| WO | WO 01/68836 | 9/2001 |
| WO | WO 01/75164 | 10/2001 |

OTHER PUBLICATIONS

Sun et al. (Biochemistry, 2001 vol. 40:14976-14984).*
Agami, Reuven, *Curr. Opin. In Chem. Bio.* 6: 829-834 (2002).
Blaszczyk, Jaroslaw, et al., Cryst*Structure* 9:1225-1236 (2001).

(Continued)

*Primary Examiner*—Tracy Vivlemore
*Assistant Examiner*—Terra Cotta Gibbs
(74) *Attorney, Agent, or Firm*—Harriet M. Strimpel; D. Phil

(57) ABSTRACT

Compositions and methods are provided for preparing an hsiRNA mixture and for silencing of gene expression in vivo. The composition relates to a mutant RnaseIII. The methods are directed to reacting a preparation of dsRNA with an effective amount of a mutant RNAse III to produce the hsiRNA mixture.

2 Claims, 17 Drawing Sheets

RNAse III class proteins

RCD - RNAse III RNA cleavage domain
RBD - RNAse III dsRNA binding domain

Structure, 9, p. 1225, (2001)

OTHER PUBLICATIONS

Byrom, Mike, et al., *Ambion Technotes Newsletter* 10:1, 4-7 (2003).
Caplen, Natasha, *Gene Therapy*, 3: 575-586 (2003).
Coburn, Glen, et al., *J. Anti. Chemo.* 51: 753-756 (2003).
Sun, Weimei et al., *Biochemistry*, 40: 5102-5110 (2001).
Wianny, Florence, et al., *Nat. Cell Biol.* 2:70-25, 25-33 (2000).
Yang, Shicheng, et al., *Mol. Cell. Biol.* 21:7807-7816 (2001).
Yang, Dun, et al., *Proc. Nat'l. Acad. Sci. USA* 99:9942-9947 (2002).

* cited by examiner

Figure 2

RNAse Activity of E38A

RNAse Activity of E38A

RNAse Activity of E38A

RNAse Activity of E38A

RNAse Activity of E38A

RNAse Activity of E65A

RNAse Activity of E38T & E38W

Figure 12

*E. coli* RNAse III Mutants

| | | 37 | | 63 | | 107 |
|---|---|---|---|---|---|---|
| Aquifex aeolicus | wt | 37 ETLEFLGDA | | 63 REGFLS | | 107 DVFEAL |
| E. coli | wt | 38 ERLEFLGDS | | 64 DEGDMS | | 114 DTVEAL |
| E38D | wt | 38 DRLEFLGDS | | 64 DEGDMS | | 114 DTVEAL |
| E38K | wt | 38 KRLEFLGDS | | 64 DEGDMS | | 114 DTVEAL |
| E38Q | wt | 38 QRLEFLGDS | | 64 DEGDMS | | 114 DTVEAL |
| E38P | wt | 38 PRLEFLGDS | | 64 DEGDMS | | 114 DTVEAL |
| E38V | wt | 38 VRLEFLGDS | | 64 DEGDMS | | 114 DTVEAL |
| E38A | 23 | 38 ARLEFLGDS | | 64 DEGDMS | | 114 DTVEAL |
| E38T | 23 | 38 TRLEFLGDS | | 64 DEGDMS | | 114 DTVEAL |
| E38W | 23 | 38 WRLEFLGDS | | 64 DEGDMS | | 114 DTVEAL |
| D45V | wt | 38 ERLEFLGVS | | 64 DEGDMS | | 114 DTVEAL |
| D45A | i | 38 ERLEFLGAS | | 64 DEGDMS | | 114 DTVEAL |
| E65P | wt | 38 ERLEFLGDS | | 64 DPGDMS | | 114 DTVEAL |
| E65A | 23 | 38 ERLEFLGDS | | 64 DAGDMS | | 114 DTVEAL |
| E117D | i | 38 ERLEFLGDS | | 64 DEGDMS | | 114 DTVDAL |
| E38Q,E65P | wt | 38 QRLEFLGDS | | 64 DPGDMS | | 114 DTVEAL |
| E38A,E65A | wt | 38 ARLEFLGDS | | 64 DAGDMS | | 114 DTVEAL |

E117D, E38A mixtures produce multimers of 23 bp product

E117D, E38A mixtures produce multimers of 23 bp product

E117D, WT mixtures produce multimers of 23 bp product siRNA evaluation tool (EXPERIMENTAL) v0.57 results - Thu Jan 13 15:59:54 2005

| | |
|---|---|
| Query: NM_000546 | Homo sapiens tumor protein p53 (Li-Fraumeni syndrome) (TP53), mRNA. |
| Query Length: | 2629 nt |
| Displayed Region: | 1 - 2608 |
| Database Searched: | Homo_sapiens -- NCBI :: hs.fna |
| Min Match Length: | 21 nt |

Hits to the following DB sequences were filtered out of the results (user cutoff 1.0E-70):
gi|8400737|ref|NM_000546.2| E-val:0.0

Current resolution is 4 base(s).

SEQUENCE LISTING

```
<160> NUMBER OF SEQ ID NOS: 26

<210> SEQ ID NO 1
<211> LENGTH: 31
<212> TYPE: DNA
<213> ORGANISM: unknown
<220> FEATURE:
<223> OTHER INFORMATION: primer

<400> SEQUENCE: 1
acaggatccc atgaacccca tcgtaattaa t                              31

<210> SEQ ID NO 2
<211> LENGTH: 36
<212> TYPE: DNA
<213> ORGANISM: unknown
<220> FEATURE:
<223> OTHER INFORMATION: primer

<400> SEQUENCE: 2
acaggatcct ctagagtcat tccagctcca gttttt                         36

<210> SEQ ID NO 3
<211> LENGTH: 26
<212> TYPE: DNA
<213> ORGANISM: unknown
<220> FEATURE:
<223> OTHER INFORMATION: primer

<400> SEQUENCE: 3
cagtaaacat aacgcgcgtt tagaat                                    26

<210> SEQ ID NO 4
<211> LENGTH: 26
<212> TYPE: DNA
<213> ORGANISM: unknown
<220> FEATURE:
<223> OTHER INFORMATION: primer

<400> SEQUENCE: 4
aattctaaac gcgcgttatg tttact                                    26

<210> SEQ ID NO 5
<211> LENGTH: 31
<212> TYPE: DNA
<213> ORGANISM: unknown
<220> FEATURE:
<223> OTHER INFORMATION: primer

<400> SEQUENCE: 5
ctcgtgtgga tgcaggcgat atgagccgga t                              31

<210> SEQ ID NO 6
<211> LENGTH: 33
<212> TYPE: DNA
```

```
<213> ORGANISM: unknown
<220> FEATURE:
<223> OTHER INFORMATION: primer

<400> SEQUENCE: 6
tccggctcat atcgcctgca tccacacgag gga                          33

<210> SEQ ID NO 7
<211> LENGTH: 20
<212> TYPE: DNA
<213> ORGANISM: unknown
<220> FEATURE:
<223> OTHER INFORMATION: primer

<400> SEQUENCE: 7
taatacgact cactataggg                                         20

<210> SEQ ID NO 8
<211> LENGTH: 38
<212> TYPE: DNA
<213> ORGANISM: unknown
<220> FEATURE:
<223> OTHER INFORMATION: primer

<400> SEQUENCE: 8
taatacgact cactatagaa ggacagatgg ttaagtac                     38

<210> SEQ ID NO 9
<211> LENGTH: 225
<212> TYPE: PRT
<213> ORGANISM: unknown
<220> FEATURE:
<223> OTHER INFORMATION: relevant region from Pasteurella multocida

<400> SEQUENCE: 9
```

Met Thr Gln Asn Leu Glu Arg Leu Gln Arg Gln Ile Gly Tyr Gln Phe
1               5                   10                  15

Asn Gln Pro Ala Leu Leu Lys Gln Ala Leu Thr His Arg Ser Ala Ala
            20                  25                  30

Val Lys His Asn Glu Arg Leu Glu Phe Leu Gly Asp Ala Ile Leu Asn
        35                  40                  45

Phe Ile Ile Ala Glu Ala Leu Tyr His Gln Phe Pro Lys Cys Asn Glu
    50                  55                  60

Gly Glu Leu Ser Arg Met Arg Ala Thr Leu Val Arg Glu Pro Thr Leu
65                  70                  75                  80

Ala Ser Leu Ala Arg Gln Phe Glu Leu Gly Asp Tyr Leu Ser Leu Gly
                85                  90                  95

Pro Gly Glu Leu Lys Ser Gly Gly Phe Arg Arg Glu Ser Ile Leu Ala
            100                 105                 110

Asp Cys Val Glu Ala Ile Ile Gly Ala Ile Ser Leu Asp Ser Asp Leu
        115                 120                 125

Ala Thr Thr Thr Lys Ile Val Gln His Trp Tyr Gln Ala Gln Leu Lys
    130                 135                 140

Gln Ile Gln Pro Gly Asp Asn Lys Asp Pro Lys Thr Arg Leu Gln
145                 150                 155                 160

Glu Tyr Leu Gln Gly Lys Arg Leu Pro Leu Pro Thr Tyr Asn Val Val
                165                 170                 175

Glu Ile Lys Gly Glu Ala His Cys Gln Thr Phe Thr Val Glu Cys Tyr
            180                 185                 190

Val Lys Asn Ile Asp Arg Thr Phe Met Gly Ser Gly Ala Ser Arg Arg

```
                195                 200                 205
Lys Ala Glu Gln Ala Ala Glu Lys Ile Leu Gln Leu Leu Glu Met
    210                 215                 220

Lys
225

<210> SEQ ID NO 10
<211> LENGTH: 227
<212> TYPE: PRT
<213> ORGANISM: unknown
<220> FEATURE:
<223> OTHER INFORMATION: relevant region from H. Influenzae

<400> SEQUENCE: 10

Met Asn His Leu Asp Arg Leu Glu Arg Lys Ile Gly Tyr Arg Phe Asn
1               5                  10                  15

Asp Ile Ala Leu Leu Lys Gln Ala Leu Thr His Arg Ser Ala Ala Thr
            20                  25                  30

Gln His Asn Glu Arg Leu Glu Phe Leu Gly Asp Ser Ile Leu Asn Phe
        35                  40                  45

Thr Ile Ala Glu Ala Leu Tyr His Gln Phe Pro Arg Cys Asn Glu Gly
    50                  55                  60

Glu Leu Ser Arg Met Arg Ala Thr Leu Val Arg Glu Pro Thr Leu Ala
65                  70                  75                  80

Ile Leu Ala Arg Gln Phe Glu Leu Gly Asp Tyr Met Ser Leu Gly Ser
                85                  90                  95

Gly Glu Leu Lys Asn Gly Gly Phe Arg Arg Glu Ser Ile Leu Ala Asp
            100                 105                 110

Cys Val Glu Ala Ile Ile Gly Ala Met Ser Leu Asp Gln Gly Leu Ala
        115                 120                 125

Val Thr Thr Gln Val Ile Arg Asn Trp Tyr Gln Gln Leu Leu Ala Glu
    130                 135                 140

Ile Lys Pro Gly Asp Asn Gln Lys Asp Ala Lys Thr Arg Leu Gln Glu
145                 150                 155                 160

Tyr Leu Gln Gly Lys His Leu Pro Leu Pro Thr Tyr Glu Val Val Asn
                165                 170                 175

Ile Gln Gly Glu Ala His Cys Gln Ile Phe Thr Val Lys Cys Lys Val
            180                 185                 190

Lys Ser Ala Glu Lys Ile Asp Arg Thr Phe Val Ala Lys Gly Ser Ser
        195                 200                 205

Arg Arg Lys Ala Glu Gln Ala Ala Glu Gln Ile Leu Lys Glu Leu
    210                 215                 220

Asp Ile Lys
225

<210> SEQ ID NO 11
<211> LENGTH: 224
<212> TYPE: PRT
<213> ORGANISM: unknown
<220> FEATURE:
<223> OTHER INFORMATION: relevant region from S. typhimurium

<400> SEQUENCE: 11

Met Asn Pro Ile Val Ile Asn Arg Leu Gln Arg Lys Leu Gly Tyr Thr
1               5                  10                  15

Phe Asn His Gln Glu Leu Leu Gln Gln Ala Leu Thr His Arg Ser Ala
            20                  25                  30
```

```
Ser Ser Lys His Asn Glu Arg Leu Glu Phe Leu Gly Asp Ser Ile Leu
        35                  40                  45

Ser Phe Val Ile Ala Asn Ala Leu Ser Arg Phe Pro Arg Val Asp Glu
 50                  55                  60

Gly Asp Met Ser Arg Met Arg Asp Pro Leu Val Arg Gly Asn Thr Leu
65                  70                  75                  80

Ala Glu Leu Ala Arg Glu Phe Asp Leu Gly Glu Cys Leu Arg Leu Gly
                85                  90                  95

Pro Gly Glu Leu Lys Ser Gly Gly Phe Arg Arg Glu Ser Ile Leu Ala
                100                 105                 110

Asp Thr Val Glu Ala Leu Ile Gly Gly Val Phe Leu Asp Ser Asn Ile
                115                 120                 125

Gln Thr Val Glu Gln Leu Ile Leu Asn Trp Tyr Lys Thr Arg Leu Asp
130                 135                 140

Glu Ile Ser Pro Gly Asp Lys Gln Lys Asp Pro Lys Thr Arg Leu Gln
145                 150                 155                 160

Glu Tyr Leu Gln Gly Arg His Leu Pro Leu Pro Ser Tyr Leu Val Val
                165                 170                 175

Gln Val Arg Gly Glu Ala His Asp Gln Glu Phe Thr Ile His Cys Gln
                180                 185                 190

Val Ser Gly Leu Ser Glu Pro Val Val Gly Thr Gly Ser Ser Arg Arg
                195                 200                 205

Lys Ala Glu Gln Ala Ala Ala Asn Ser Val Lys Lys Leu Glu Leu Glu
                210                 215                 220

<210> SEQ ID NO 12
<211> LENGTH: 226
<212> TYPE: PRT
<213> ORGANISM: unknown
<220> FEATURE:
<223> OTHER INFORMATION: relevant region from E. coli

<400> SEQUENCE: 12

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
                20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
 50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
                100                 105                 110

Ala Asp Thr Val Glu Ala Leu Ile Gly Gly Val Phe Leu Asp Ser Asp
                115                 120                 125

Ile Gln Thr Val Glu Lys Leu Ile Leu Asn Trp Tyr Gln Thr Arg Leu
130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175
```

```
Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Glu Gln Ala Leu Lys Lys Leu Glu
    210                 215                 220

Leu Glu
225

<210> SEQ ID NO 13
<211> LENGTH: 225
<212> TYPE: PRT
<213> ORGANISM: unknown
<220> FEATURE:
<223> OTHER INFORMATION: relevant region from V. cholerae

<400> SEQUENCE: 13

Met Thr Pro Pro Met Asn Lys Leu Thr Ser Lys Leu Gly Tyr Thr Phe
1               5                   10                  15

Lys Glu Thr Glu Leu Leu Asn Leu Ala Leu Thr His Arg Ser Ala Asn
            20                  25                  30

Gly Lys His Asn Glu Arg Leu Glu Phe Leu Gly Asp Ser Ile Leu Ser
        35                  40                  45

Phe Val Ile Ala Asp Glu Leu Tyr Arg Arg Phe Pro Lys Val Asn Glu
    50                  55                  60

Gly Asp Met Ser Arg Met Arg Ala Thr Leu Val Arg Gly Asn Thr Leu
65                  70                  75                  80

Ala Glu Leu Gly Arg Glu Phe Asp Leu Gly Asp Tyr Leu Lys Leu Gly
                85                  90                  95

Pro Gly Glu Leu Lys Ser Gly Gly Phe Arg Arg Asp Ser Ile Leu Ala
            100                 105                 110

Asp Ala Val Glu Ala Ile Ile Gly Ala Ile Tyr Leu Asp Ser Asp Leu
        115                 120                 125

Glu Thr Ala Arg Ser Ile Val Leu Glu Trp Tyr His Gly Arg Leu Glu
130                 135                 140

Glu Ile Lys Pro Gly Ala Ser Gln Lys Asp Pro Lys Thr Arg Leu Gln
145                 150                 155                 160

Glu Phe Leu Gln Gly Arg Arg Lys Pro Leu Pro Val Tyr Thr Val Thr
                165                 170                 175

Asn Ile Lys Gly Glu Ala His Asn Gln Glu Phe Thr Val Ala Cys Glu
            180                 185                 190

Val Ala Gly Met Asp Thr Pro Val Ile Gly Lys Gly Thr Ser Arg Arg
        195                 200                 205

Lys Ala Glu Gln Ala Ala Ala Glu Thr Ala Leu Glu Gln Leu Thr Asn
    210                 215                 220

Gly
225

<210> SEQ ID NO 14
<211> LENGTH: 229
<212> TYPE: PRT
<213> ORGANISM: unknown
<220> FEATURE:
<223> OTHER INFORMATION: relevant region from P. seruginosa

<400> SEQUENCE: 14

Met Ser Asn Ser Leu Asp Arg Leu Glu Arg Lys Leu Gly Tyr Thr Phe
1               5                   10                  15
```

```
Lys Asp Arg Asp Leu Met Val Leu Ala Leu Thr His Arg Ser Tyr Ala
            20                  25                  30

Gly Arg Asn Asn Glu Arg Leu Glu Phe Leu Gly Asp Ala Ile Leu Asn
            35                  40                  45

Phe Val Ile Gly Glu Ala Leu Phe His His Phe Pro Gln Ala Arg Glu
            50                  55                  60

Gly Gln Leu Ser Arg Leu Arg Ala Arg Leu Val Lys Gly Glu Thr Leu
65                  70                  75                  80

Ala Leu Leu Ala Arg Gly Phe Glu Val Gly Asp Tyr Leu Arg Leu Gly
            85                  90                  95

Ser Gly Glu Leu Lys Ser Gly Gly Phe Arg Arg Glu Ser Ile Leu Ala
            100                 105                 110

Asp Ala Met Glu Ala Leu Ile Gly Ala Ile Tyr Leu Asp Thr Gly Met
            115                 120                 125

Asp Ser Ala Arg Glu Arg Ile Ile Ala Trp Leu Gly Pro Gln Leu Arg
            130                 135                 140

Glu Leu Thr Pro Val Asp Thr Asn Lys Asp Pro Lys Thr Arg Leu Gln
145                 150                 155                 160

Glu Phe Leu Gln Ser Arg Gly Cys Asp Leu Pro Arg Tyr Glu Val Val
            165                 170                 175

Asp Ile Gln Gly Glu Pro His Cys Arg Thr Phe Phe Val Asp Cys Glu
            180                 185                 190

Val Ala Leu Leu Ser Asp Lys Thr His Gly His Gly Gly Ser Arg Arg
            195                 200                 205

Ile Ala Glu Gln Val Ala Ala Ala Ala Leu Val Ala Leu Gly Val
            210                 215                 220

Glu Asn Gly His Asp
225

<210> SEQ ID NO 15
<211> LENGTH: 239
<212> TYPE: PRT
<213> ORGANISM: unknown
<220> FEATURE:
<223> OTHER INFORMATION: relevant region from H. pylori

<400> SEQUENCE: 15

Met Lys Asn Lys Arg Ser Gln Asn Ser Pro Tyr Val Thr Pro Asp Asn
1               5                   10                  15

Pro Tyr Leu Thr Leu Glu Lys Ala Leu Gly Tyr Ser Phe Lys Asp Lys
            20                  25                  30

Arg Leu Leu Glu Gln Ala Leu Thr His Lys Ser Cys Lys Leu Ala Leu
            35                  40                  45

Asn Asn Glu Arg Leu Glu Phe Leu Gly Asp Ala Val Leu Gly Leu Val
            50                  55                  60

Ile Gly Glu Leu Leu Tyr His Lys Phe Tyr Gln Tyr Asp Glu Gly Lys
65                  70                  75                  80

Leu Ser Lys Leu Arg Ala Ser Ile Val Ser Ala His Gly Phe Thr Lys
            85                  90                  95

Leu Ala Lys Ala Ile Ala Leu Gln Asp Tyr Leu Arg Val Ser Ser Ser
            100                 105                 110

Glu Glu Ile Ser Lys Gly Arg Glu Lys Pro Ser Ile Leu Ser Ser Ala
            115                 120                 125

Phe Glu Ala Leu Met Ala Gly Val Tyr Leu Glu Ala Gly Leu Ala Lys
            130                 135                 140
```

```
Val Arg Lys Ile Ile Gln Asn Leu Leu Asn Arg Ala Tyr Lys Arg Leu
145                 150                 155                 160

Asp Leu Glu His Leu Phe Met Asp Tyr Lys Thr Ala Leu Gln Glu Leu
            165                 170                 175

Thr Gln Ala Gln Phe Cys Val Ile Pro Thr Tyr Gln Leu Leu Gln Glu
        180                 185                 190

Lys Gly Pro Asp His His Lys Glu Phe Glu Met Ala Leu Tyr Ile Gln
        195                 200                 205

Asp Lys Met Tyr Ala Thr Ala Lys Gly Lys Ser Lys Lys Glu Ala Glu
        210                 215                 220

Gln Gln Cys Ala Tyr Gln Ala Leu Gln Lys Leu Lys Glu Ala Lys
225                 230                 235

<210> SEQ ID NO 16
<211> LENGTH: 230
<212> TYPE: PRT
<213> ORGANISM: unknown
<220> FEATURE:
<223> OTHER INFORMATION: relevant region from S. pyogenes

<400> SEQUENCE: 16

Met Lys Gln Leu Glu Glu Leu Leu Ser Thr Ser Phe Asp Ile Gln Phe
1               5                   10                  15

Asn Asp Leu Thr Leu Leu Glu Thr Ala Phe Thr His Thr Ser Tyr Ala
            20                  25                  30

Asn Glu His Arg Leu Leu Asn Val Ser His Asn Glu Arg Leu Glu Phe
        35                  40                  45

Leu Gly Asp Ala Val Leu Gln Leu Ile Ile Ser Glu Tyr Leu Phe Ala
    50                  55                  60

Lys Tyr Pro Lys Lys Thr Glu Gly Asp Met Ser Lys Leu Arg Ser Met
65                  70                  75                  80

Ile Val Arg Glu Glu Ser Leu Ala Gly Phe Ser Arg Phe Cys Ser Phe
                85                  90                  95

Asp Ala Tyr Ile Lys Leu Gly Lys Gly Glu Glu Lys Ser Gly Gly Arg
            100                 105                 110

Arg Arg Asp Thr Ile Leu Gly Asp Leu Phe Glu Ala Phe Leu Gly Ala
        115                 120                 125

Leu Leu Leu Asp Lys Gly Ile Asp Ala Val Arg Arg Phe Leu Lys Gln
    130                 135                 140

Val Met Ile Pro Gln Val Glu Lys Gly Asn Phe Glu Arg Val Lys Asp
145                 150                 155                 160

Tyr Lys Thr Cys Leu Gln Glu Phe Leu Gln Thr Lys Gly Asp Val Ala
                165                 170                 175

Ile Asp Tyr Gln Val Ile Ser Glu Lys Gly Pro Ala His Ala Lys Gln
            180                 185                 190

Phe Glu Val Ser Ile Val Val Asn Gly Ala Val Leu Ser Lys Gly Leu
        195                 200                 205

Gly Lys Ser Lys Lys Leu Ala Glu Gln Asp Ala Ala Lys Asn Ala Leu
    210                 215                 220

Ala Gln Leu Ser Glu Val
225                 230

<210> SEQ ID NO 17
<211> LENGTH: 232
<212> TYPE: PRT
<213> ORGANISM: unknown
```

-continued

```
<220> FEATURE:
<223> OTHER INFORMATION: relevant region from S. pneumoniae

<400> SEQUENCE: 17

Met Lys Glu Leu Gln Thr Val Leu Lys Asn His Phe Ala Ile Glu Phe
1               5                   10                  15

Ala Asp Lys Lys Leu Leu Glu Thr Ala Phe Thr His Thr Ser Tyr Ala
            20                  25                  30

Asn Glu His Arg Leu Leu Lys Ile Ser His Asn Glu Arg Leu Glu Phe
        35                  40                  45

Leu Gly Asp Ala Val Leu Gln Leu Leu Ile Ser Glu Tyr Leu Tyr Lys
    50                  55                  60

Lys Tyr Pro Lys Lys Pro Glu Gly Asp Leu Ser Lys Leu Arg Ala Met
65                  70                  75                  80

Ile Val Arg Glu Glu Ser Leu Ala Gly Phe Ala Arg Asp Cys Gln Phe
                85                  90                  95

Asp Gln Phe Ile Lys Leu Gly Lys Gly Glu Lys Ser Gly Gly Arg
            100                 105                 110

Asn Arg Asp Thr Ile Leu Gly Asp Ala Phe Glu Ala Phe Leu Gly Ala
        115                 120                 125

Leu Leu Leu Asp Lys Asp Val Ala Lys Val Lys Glu Phe Ile Tyr Gln
    130                 135                 140

Val Met Ile Pro Lys Val Glu Ala Gly Glu Phe Glu Met Ile Thr Asp
145                 150                 155                 160

Tyr Lys Thr His Leu Gln Glu Leu Leu Gln Val Asn Gly Asp Val Ala
                165                 170                 175

Ile Arg Tyr Gln Val Ile Ser Glu Thr Gly Pro Ala His Asp Lys Val
            180                 185                 190

Phe Asp Val Glu Val Leu Val Glu Gly Lys Ser Ile Gly Gln Gly Gln
        195                 200                 205

Gly Arg Ser Lys Lys Leu Ala Glu Gln Glu Ala Ala Lys Asn Ala Val
    210                 215                 220

Glu Lys Gly Leu Asp Ser Cys Ile
225                 230

<210> SEQ ID NO 18
<211> LENGTH: 266
<212> TYPE: PRT
<213> ORGANISM: unknown
<220> FEATURE:
<223> OTHER INFORMATION: relevant region from B. subtilis

<400> SEQUENCE: 18

Met Ser Lys His Ser His Tyr Lys Asp Lys Lys Phe Tyr Lys
1               5                   10                  15

Val Glu Gln Phe Lys Glu Phe Gln Glu Arg Ile Ser Val His Phe Gln
            20                  25                  30

Asn Glu Lys Leu Leu Tyr Gln Ala Phe Thr His Ser Ser Tyr Val Asn
        35                  40                  45

Glu His Arg Lys Lys Pro Tyr Glu Asp Asn Glu Arg Leu Glu Phe Leu
    50                  55                  60

Gly Asp Ala Val Leu Glu Leu Thr Ile Ser Arg Phe Leu Phe Pro Lys
65                  70                  75                  80

Tyr Pro Ala Met Ser Glu Gly Asp Leu Thr Lys Leu Arg Ala Ala Ile
                85                  90                  95

Val Cys Glu Pro Ser Leu Val Ser Leu Ala His Glu Leu Ser Phe Gly
```

-continued

```
                100                 105                 110
Asp Leu Val Leu Leu Gly Lys Gly Glu Glu Met Thr Gly Gly Arg Lys
            115                 120                 125

Arg Pro Ala Leu Leu Ala Asp Val Phe Glu Ala Phe Ile Gly Ala Leu
        130                 135                 140

Tyr Leu Asp Gln Gly Leu Glu Pro Val Glu Ser Phe Leu Lys Val Tyr
145                 150                 155                 160

Val Phe Pro Lys Ile Asn Asp Gly Ala Phe Pro His Val Met Asp Phe
                165                 170                 175

Lys Ser Gln Leu Gln Glu Tyr Val Gln Arg Asp Gly Lys Gly Ser Leu
            180                 185                 190

Glu Tyr Lys Ile Ser Asn Glu Lys Gly Pro Ala His Asn Arg Glu Phe
        195                 200                 205

Glu Ala Ile Val Ser Leu Lys Gly Glu Pro Leu Gly Val Gly Asn Gly
    210                 215                 220

Arg Ser Lys Lys Glu Ala Glu Gln His Ala Ala Gln Glu Ala Leu Ala
225                 230                 235                 240

Lys Leu Glu Lys His His Thr Lys Gln Leu Asn Pro Pro Tyr Asp Ser
                245                 250                 255

Gly Gly Phe Gln Tyr Val Cys Arg Leu Ile
            260                 265
```

<210> SEQ ID NO 19
<211> LENGTH: 243
<212> TYPE: PRT
<213> ORGANISM: unknown
<220> FEATURE:
<223> OTHER INFORMATION: relevant region from S. aureus

<400> SEQUENCE: 19

```
Met Ser Lys Gln Lys Ser Glu Ile Val Asn Arg Phe Arg Lys Arg
1               5                   10                  15

Phe Asp Thr Lys Met Thr Glu Leu Gly Phe Thr Tyr Gln Asn Ile Asp
                20                  25                  30

Leu Tyr Gln Gln Ala Phe Ser His Ser Ser Phe Ile Asn Asp Phe Asn
            35                  40                  45

Met Asn Arg Leu Asp His Asn Glu Arg Leu Glu Phe Leu Gly Asp Ala
        50                  55                  60

Val Leu Glu Leu Thr Val Ser Arg Tyr Leu Phe Asp Lys His Pro Asn
65                  70                  75                  80

Leu Pro Glu Gly Asn Leu Thr Lys Met Arg Ala Thr Ile Val Cys Glu
                85                  90                  95

Pro Ser Leu Val Ile Phe Ala Asn Lys Ile Gly Leu Asn Glu Met Ile
            100                 105                 110

Leu Leu Gly Lys Gly Glu Glu Lys Thr Gly Gly Arg Thr Arg Pro Ser
        115                 120                 125

Leu Ile Ser Asp Ala Phe Glu Ala Phe Ile Gly Ala Leu Tyr Leu Asp
    130                 135                 140

Gln Gly Leu Asp Ile Val Trp Lys Phe Ala Lys Val Ile Phe Pro
145                 150                 155                 160

His Val Glu Gln Asn Glu Leu Leu Gly Val Val Asp Phe Lys Thr Gln
                165                 170                 175

Phe Gln Glu Tyr Val His Gln Asn Lys Gly Asp Val Thr Tyr Asn
            180                 185                 190

Leu Ile Lys Glu Glu Gly Pro Ala His His Arg Leu Phe Thr Ser Glu
```

```
                195                 200                 205
Val Ile Leu Gln Gly Glu Ala Ile Ala Glu Gly Lys Gly Lys Thr Lys
    210                 215                 220

Lys Glu Ser Glu Gln Arg Ala Ala Glu Ser Ala Tyr Lys Gln Leu Lys
225                 230                 235                 240

Gln Ile Lys

<210> SEQ ID NO 20
<211> LENGTH: 246
<212> TYPE: PRT
<213> ORGANISM: unknown
<220> FEATURE:
<223> OTHER INFORMATION: relevant region from Borella burgdorferi

<400> SEQUENCE: 20

Met Met Lys Lys Lys Ser Ser Asp Phe Cys Leu Cys Asn Glu Arg Lys
1               5                   10                  15

Ser Gln Leu Ser Lys Phe Leu Glu Asn Leu Ser Ile Asp Phe Ser Asn
            20                  25                  30

Phe Asp Leu Leu Asn Thr Ala Leu Cys His Ser Ser Tyr Ser Asn Glu
        35                  40                  45

Leu Asp Gln Lys Ser Ser Asn Asn Glu Arg Leu Glu Phe Leu Gly Asp
    50                  55                  60

Ser Val Leu Asn Leu Ile Ile Thr Asp His Leu Tyr Lys Thr Tyr Pro
65                  70                  75                  80

Asn Lys Ser Glu Gly Glu Leu Ser Lys Ala Arg Ser Tyr Ile Val Ser
                85                  90                  95

Glu Asp Ser Leu Ser Asn Ile Ala Arg Glu Ile Asn Leu Gly Ser Tyr
            100                 105                 110

Ile Leu Leu Gly Arg Gly Glu Glu Ser Asn Asp Gly Arg Asn Lys Lys
        115                 120                 125

Gly Ile Leu Ala Asp Ala Ile Glu Ala Phe Val Gly Ala Ile Tyr Leu
    130                 135                 140

Asp Ser Gly Phe Ser Arg Ala Thr Glu Phe Val Val Gly Leu Phe Asp
145                 150                 155                 160

Met Tyr Ile Arg Leu Met Phe Asn Arg Gly Asp Phe Lys Asp Tyr Lys
                165                 170                 175

Ser Leu Leu Gln Glu Tyr Val Gln Lys Lys Tyr Lys Ile Ser Pro Ser
            180                 185                 190

Tyr Lys Leu Asp Lys Glu Ile Gly Pro Asp His Asp Lys Val Phe Cys
        195                 200                 205

Val Glu Leu Tyr Val Gly Glu Asn Phe Ile Ser Asn Gly Lys Gly Lys
    210                 215                 220

Ser Lys Lys Glu Ala Glu Met Arg Ala Ala Glu Val Ala Leu Lys Ala
225                 230                 235                 240

Met Glu Asn Ile Asn Leu
                245

<210> SEQ ID NO 21
<211> LENGTH: 238
<212> TYPE: PRT
<213> ORGANISM: unknown
<220> FEATURE:
<223> OTHER INFORMATION: relevant region from M. leprae

<400> SEQUENCE: 21

Met Thr Gln Pro Arg Gln Ala Leu Leu Asp Ala Phe Gly Val Asp Leu
```

-continued

```
1               5                   10                  15

Pro Asp Glu Leu Leu Ser Leu Ala Leu Thr His Arg Ser Tyr Ala Tyr
            20                  25                  30

Glu His Gly Gly Leu Pro Thr Asn Glu Arg Leu Glu Phe Leu Gly Asp
            35                  40                  45

Ala Val Leu Ser Leu Thr Ile Thr Asp Glu Leu Phe His Arg His Pro
            50                  55                  60

Asp Arg Ser Glu Gly Asp Leu Ala Lys Leu Arg Ala Ser Val Val Asn
65                  70                  75                  80

Thr Gln Ala Leu Ala Tyr Val Ala Arg Asn Leu Ser Asp Gly Gly Leu
                85                  90                  95

Gly Val Tyr Leu Leu Gly Arg Gly Glu Thr Asn Thr Gly Gly Ala
            100                 105                 110

Asp Lys Ser Ser Ile Leu Ala Asp Gly Met Glu Ser Leu Leu Gly Ala
            115                 120                 125

Ile Tyr Leu His His Gly Ile Glu Val Ala Arg Gln Val Ile Leu Arg
            130                 135                 140

Leu Phe Gly Thr Leu Leu Asp Ala Ala Pro Thr Leu Gly Ala Gly Leu
145                 150                 155                 160

Asp Trp Lys Thr Ser Leu Gln Glu Leu Thr Ala Ala Arg Gly Met Gly
                165                 170                 175

Val Pro Ser Tyr Val Val Thr Ser Thr Gly Pro Asp His Asp Lys Glu
                180                 185                 190

Phe Thr Ala Val Val Val Met Asp Thr Glu Tyr Gly Ser Gly Ile
                195                 200                 205

Gly His Ser Lys Lys Glu Ala Glu Gln Lys Ala Ala Ser Ala Ala Trp
            210                 215                 220

Lys Ala Leu Asp Val Leu Gly Val Gly Lys Thr Ser Val
225                 230                 235
```

<210> SEQ ID NO 22
<211> LENGTH: 221
<212> TYPE: PRT
<213> ORGANISM: unknown
<220> FEATURE:
<223> OTHER INFORMATION: relevant region from Aquifex aeolicus

<400> SEQUENCE: 22

```
Met Lys Met Leu Glu Gln Leu Glu Lys Lys Leu Gly Tyr Thr Phe Lys
1               5                   10                  15

Asp Lys Ser Leu Leu Glu Lys Ala Leu Thr His Val Ser Tyr Ser Lys
            20                  25                  30

Lys Glu His Tyr Glu Thr Leu Glu Phe Leu Gly Asp Ala Leu Val Asn
            35                  40                  45

Phe Phe Ile Val Asp Leu Leu Val Gln Tyr Ser Pro Asn Lys Arg Glu
            50                  55                  60

Gly Phe Leu Ser Pro Leu Lys Ala Tyr Leu Ile Ser Glu Glu Phe Phe
65                  70                  75                  80

Asn Leu Leu Ala Gln Lys Leu Glu Leu His Lys Phe Ile Arg Ile Lys
                85                  90                  95

Arg Gly Lys Ile Asn Glu Thr Ile Ile Gly Asp Val Phe Glu Ala Leu
            100                 105                 110

Trp Ala Ala Val Tyr Ile Asp Ser Gly Arg Asp Ala Asn Phe Thr Arg
            115                 120                 125

Glu Leu Phe Tyr Lys Leu Phe Lys Glu Asp Ile Leu Ser Ala Ile Lys
```

```
                130                 135                 140
Glu Gly Arg Val Lys Lys Asp Tyr Lys Thr Ile Leu Gln Glu Ile Thr
145                 150                 155                 160

Gln Lys Arg Trp Lys Glu Arg Pro Tyr Arg Leu Ile Ser Val Glu
                165                 170                 175

Gly Pro His His Lys Lys Phe Ile Val Glu Ala Lys Ile Lys Glu
            180                 185                 190

Tyr Arg Thr Leu Gly Glu Gly Lys Ser Lys Lys Glu Ala Glu Gln Arg
                195                 200                 205

Ala Ala Glu Glu Leu Ile Lys Leu Leu Glu Glu Ser Glu
        210                 215                 220

<210> SEQ ID NO 23
<211> LENGTH: 227
<212> TYPE: PRT
<213> ORGANISM: unknown
<220> FEATURE:
<223> OTHER INFORMATION: relevant region from Rickettsia conoril

<400> SEQUENCE: 23

Met Glu Ser Phe Glu Lys Leu Glu Lys Leu Leu Ser Tyr Ser Phe Lys
1               5                   10                  15

Asn Lys Glu Leu Leu Ile Glu Ala Leu Ser His Pro Ser Leu Arg Gln
            20                  25                  30

His His Glu Tyr Lys Asp Asp Lys Asp Tyr Glu Arg Leu Glu Phe Leu
        35                  40                  45

Gly Asp Ala Val Leu Asn Leu Val Ile Thr Glu Ile Leu Phe Arg Asn
    50                  55                  60

Phe Ala Asn Tyr Asn Glu Gly Asn Leu Ala Lys Ile Arg Ser Tyr Leu
65                  70                  75                  80

Val Cys Lys Glu Thr Ile Cys Met Val Gly Ala Lys Leu Thr Leu Lys
                85                  90                  95

Asn Tyr Ile Ile Met Thr His Gly Glu Glu Val Ala Gly Gly Arg Asp
            100                 105                 110

Asn Leu Asn Asn Ile Glu Asn Ala Thr Glu Ala Leu Ile Ala Ala Ile
        115                 120                 125

Tyr Leu Asp Ser Asn Ile Glu Thr Thr His Asp Ile Ile Glu Asn Leu
    130                 135                 140

Trp Ala Glu Phe Ile Lys Val Gln Asn Leu Thr Asp Tyr Asp Pro Lys
145                 150                 155                 160

Thr Ala Leu Gln Glu Trp Ala Gln Ala Ser Asp His His Leu Pro Ile
                165                 170                 175

Tyr Arg Leu Ile Lys Arg Glu Gly Ala Ser His Ser Ser Thr Phe Thr
            180                 185                 190

Val Leu Val Lys Val Lys Asp Tyr Glu Gln Thr Gly Thr Gly His Thr
        195                 200                 205

Ile Lys Glu Ala Glu Lys Asn Ala Ala Arg Ser Leu Leu His Arg Leu
    210                 215                 220

Lys Asn Asp
225

<210> SEQ ID NO 24
<211> LENGTH: 256
<212> TYPE: PRT
<213> ORGANISM: unknown
<220> FEATURE:
<223> OTHER INFORMATION: relevant region from A. tumefaciens
```

<400> SEQUENCE: 24

```
Met Gly Met Ala Cys Gln His Ala Leu Gly Pro Pro Val Gln Gly Cys
1               5                   10                  15

Gly Met Ser Lys Thr Lys Pro Leu Ser Ala Asp Glu Ile Ser Arg Leu
                20                  25                  30

Glu Ala Leu Ile Gly Tyr Glu Phe Lys Glu Lys Ala Arg Leu Asp Arg
            35                  40                  45

Ala Leu Thr His Ala Ser Ala Arg Ser Ala Ala Gly Asn Tyr Glu
        50                  55                  60

Arg Leu Glu Phe Leu Gly Asp Arg Val Leu Gly Leu Cys Val Ala Glu
65                  70                  75                  80

Leu Leu Phe Ser Thr Phe Arg Asn Ala Ser Glu Gly Glu Leu Ser Val
                85                  90                  95

Arg Leu Asn Gln Leu Val Ser Ala Glu Ser Cys Ala Ala Ile Gly Asp
                100                 105                 110

Glu Met Gly Leu His Asn Phe Ile Arg Thr Gly Ser Asp Val Lys Lys
            115                 120                 125

Leu Thr Gly Lys Ala Met Leu Asn Val Arg Ala Asp Val Val Glu Ser
    130                 135                 140

Leu Ile Ala Thr Leu Tyr Leu Asp Gly Gly Leu Glu Ala Ser Arg Lys
145                 150                 155                 160

Phe Ile Leu Lys Tyr Trp Gln Gly Arg Ala Thr Ser Val Asp Ala Gly
                165                 170                 175

Arg Arg Asp Ala Lys Thr Glu Leu Gln Glu Trp Ala His Ala Arg Phe
            180                 185                 190

Ala Ala Thr Pro Ala Tyr Arg Val Asp Asp Arg Ser Gly Pro Asp His
        195                 200                 205

Asp Pro Ser Phe Thr Val Thr Val Glu Ile Pro Gly Val Lys Pro Glu
    210                 215                 220

Thr Gly Val Glu Arg Ser Lys Arg Ala Ala Glu Gln Val Ala Ala Thr
225                 230                 235                 240

Arg Leu Leu Glu Arg Glu Gly Val Trp Arg Lys Ser Pro Thr Gly Asn
                245                 250                 255
```

<210> SEQ ID NO 25
<211> LENGTH: 471
<212> TYPE: PRT
<213> ORGANISM: unknown
<220> FEATURE:
<223> OTHER INFORMATION: relevant region from S. cerevisiae

<400> SEQUENCE: 25

```
Met Gly Ser Lys Val Ala Gly Lys Lys Lys Thr Gln Asn Asp Asn Lys
1               5                   10                  15

Leu Asp Asn Glu Asn Gly Ser Gln Gln Arg Glu Asn Ile Asn Thr Lys
                20                  25                  30

Thr Leu Leu Lys Gly Asn Leu Lys Ile Ser Asn Tyr Lys Tyr Leu Glu
            35                  40                  45

Val Ile Gln Leu Glu His Ala Val Thr Lys Leu Val Glu Ser Tyr Asn
        50                  55                  60

Lys Ile Ile Glu Leu Ser Pro Asn Leu Val Ala Tyr Asn Glu Ala Val
65                  70                  75                  80

Asn Asn Gln Asp Arg Val Pro Val Gln Ile Leu Pro Ser Leu Ser Arg
                85                  90                  95
```

```
Tyr Gln Leu Lys Leu Ala Ala Glu Leu Lys Thr Leu His Asp Leu Lys
            100                 105                 110

Lys Asp Ala Ile Leu Thr Glu Ile Thr Asp Tyr Glu Asn Glu Phe Asp
            115                 120                 125

Thr Glu Gln Lys Gln Pro Ile Leu Gln Glu Ile Ser Lys Ala Asp Met
        130                 135                 140

Glu Lys Leu Glu Lys Leu Glu Gln Val Lys Arg Glu Lys Arg Glu Lys
145                 150                 155                 160

Ile Asp Val Asn Val Tyr Glu Asn Leu Asn Glu Lys Glu Asp Glu Glu
                165                 170                 175

Glu Asp Glu Gly Glu Asp Ser Tyr Asp Pro Thr Lys Ala Gly Asp Ile
            180                 185                 190

Val Lys Ala Thr Lys Trp Pro Pro Lys Leu Pro Glu Ile Gln Asp Leu
            195                 200                 205

Ala Ile Arg Ala Arg Val Phe Ile His Lys Ser Thr Ile Lys Asp Lys
            210                 215                 220

Val Tyr Leu Ser Gly Ser Glu Met Ile Asn Ala His Asn Glu Arg Leu
225                 230                 235                 240

Glu Phe Leu Gly Asp Ser Ile Leu Asn Ser Val Met Thr Leu Ile Ile
                245                 250                 255

Tyr Asn Lys Phe Pro Asp Tyr Ser Glu Gly Gln Leu Ser Thr Leu Arg
            260                 265                 270

Met Asn Leu Val Ser Asn Glu Gln Ile Lys Gln Trp Ser Ile Met Tyr
        275                 280                 285

Asn Phe His Glu Lys Leu Lys Thr Asn Phe Asp Leu Lys Asp Glu Asn
            290                 295                 300

Ser Asn Phe Gln Asn Gly Lys Leu Lys Leu Tyr Ala Asp Val Phe Glu
305                 310                 315                 320

Ala Tyr Ile Gly Gly Leu Met Glu Asp Asp Pro Arg Asn Asn Leu Pro
                325                 330                 335

Lys Ile Arg Lys Trp Leu Arg Lys Leu Ala Lys Pro Val Ile Glu Glu
            340                 345                 350

Ala Thr Arg Asn Gln Val Ala Leu Glu Lys Thr Asp Lys Leu Asp Met
            355                 360                 365

Asn Ala Lys Arg Gln Leu Tyr Ser Leu Ile Gly Tyr Ala Ser Leu Arg
        370                 375                 380

Leu His Tyr Val Thr Val Lys Lys Pro Thr Ala Val Asp Pro Asn Ser
385                 390                 395                 400

Ile Val Glu Cys Arg Val Gly Asp Gly Thr Val Leu Gly Thr Gly Val
                405                 410                 415

Gly Arg Asn Ile Lys Ile Ala Gly Ile Arg Ala Ala Glu Asn Ala Leu
            420                 425                 430

Arg Asp Lys Lys Met Leu Asp Phe Tyr Ala Lys Gln Arg Ala Ala Ile
            435                 440                 445

Pro Arg Ser Glu Ser Val Leu Lys Asp Pro Ser Gln Lys Asn Lys Lys
        450                 455                 460

Arg Lys Phe Ser Asp Thr Ser
465                 470

<210> SEQ ID NO 26
<211> LENGTH: 25
<212> TYPE: DNA
<213> ORGANISM: unknown
<220> FEATURE:
<223> OTHER INFORMATION: primer
```

```
<400> SEQUENCE: 26
ctcgagtaat acgactcact atagg                                          25
```

COMPOSITIONS AND METHODS FOR GENERATING SHORT DOUBLE-STRANDED RNA USING MUTATED RNASE III

CROSS REFERENCE

This application is a §371 application of international application No. PCT/US2005/0229 filed on 21 Jan. 2005, which claims priority from U.S. provisional application No. 60/538,805 filed on 23 Jan. 2004, 60/543,880 filed on 12 Feb. 2004 and 60/572,240 filed on 18 May 2004, herein incorporated by reference.

BACKGROUND OF THE INVENTION

RNA interference (RNAi) employing short double-stranded RNA (siRNA) is a powerful tool for silencing gene expression (WO 01/29058, WO 01/68836, WO 01/75164). Large fragments of double-stranded RNA (dsRNA) elicit a non-specific response in mammalian cells through activation of the interferon (IFN) response pathway that leads to suppression of translation and cell death (Yang, et al., *Mol. Cell. Biol.* 21:7807-7816 (2001) and Wianny, et al., *Nat. Cell Biol.* 2:70-25, 25-33 (2000)). The standard method for generating siRNA is based on chemical synthesis of a pre-determined short sequence. In addition to the high cost of this method, computer models are generally required to predict the short sequences effective for RNAi experiments.

A mixture of short lengths of dsRNA obtained through partial digestion of large dsRNA with RNase III in the presence of magnesium ion buffer has been shown to "knockdown" the expression of cognate genes in cultured mammalian cell lines via RNAi (Yang, et al., *Proc. Nat'l. Acad. Sci. USA* 99:9942-9947 (2002)). However, achieving partial digestions yielding the right size range of product is often a difficult and time-consuming process and requires gel separation to obtain fragments of the desired size. Furthermore the inclusion of all possible sequences contained in the starting material is not ensured. US published application US-2004-0038278, herein incorporated by reference, describes how RNase III in the presence of transition metal ions can produce a heterogeneous mixture of fragments of a size suitable for gene silencing. This is a significant improvement on existing methods of making siRNA fragments. However, it would be desirable to increase the flexibility of the methodology for example to permit non-critical incubation times that can vary in a broad range as determined by the convenience of the experimenter and/or to increase the range of buffers that might be used to create a heterogeneous siRNA mixture.

SUMMARY

In an embodiment of the invention, a method is provided for preparing a heterogeneous siRNA (hsiRNA) mixture that includes the step of reacting a preparation of dsRNA with an effective amount of a mutant RNase III to produce the hsiRNA mixture. This reaction may occur in a magnesium or manganese buffer.

In any of the embodiments described herein, the mutant RNase III may be characterized, for example, by a mutation in the position corresponding to E38 in *E.coli* RNase III, such as E38A, E38T, E38W or by a mutation at E65, for example, E65A in *E. Coli* RNase III.

In an embodiment of the invention, a method of forming an hsiRNA preparation is described which includes the step of combining a large dsRNA with a mutant RNase III for an effective time period so as to cleave the large dsRNA to form the hsiRNA preparation wherein (i) at least 90% of the large dsRNA is cleaved as determined by gel electrophoresis and ethidium bromide staining; and (ii) at least 30% of the cleaved dsRNA which forms the hsiRNA preparation has a fragment size of 18-30 nt. The effective time period may be from about 1 min to 20 hours, for example, 10 minutes or more, 5 hours or more or 10 hours.

In any of the methods described herein, the large dsRNA has a length of at least about 50 nt.

In an embodiment of the invention, a method is provided of down-regulating gene expression of a target gene, having the following steps: (a) preparing a heterogeneous siRNA mixture containing dsRNA fragments from a preparation of large dsRNA by means of a mutant RNase III; (b) causing selected dsRNA fragments from the siRNA mixture to degrade mRNA transcribed from the target gene; and (c) down-regulating gene expression of the target gene. At least one of step (a) and (b) may occur in vivo. In those circumstances, the in vivo step occurs in a eukaryotic cell wherein the eukaryotic cell may be present in a mammal or, more generally, in a non-human animal such that reducing expression of the one or more target genes cause a phenotypic change. The phenotypic change may provide a treatment for a disease in the mammal or an enhancement of a desired characteristic in the mammal or may be diagnostic for a selected phenotype. Down-regulating gene expression can be used as a tool for analyzing a biochemical pathway in which the gene product functions. The biochemical pathway may be further analyzed in combination with a diagnostic reagent, for example, a diagnostic reagent that is one or more antibodies.

In an embodiment of the invention, step (a) of the method described above may further include combining a first hsiRNA mixture with one or more additional hsiRNA mixtures for down-regulating gene expression.

In an embodiment of the invention, a method is provided for selecting individual siRNA fragments from hsiRNA mixtures and introducing the individual siRNA fragments into a eukaryotic cell for down-regulating gene expression.

In an embodiment of the invention, an hsiRNA preparation is provided in which at least 30% of the preparation comprises fragments of a size of 18-30 nt, the preparation containing more than 10 different sequence fragments, the preparation being capable of down regulating targeted gene expression in a cell wherein the targeted gene is selected from the group consisting of Akt1, 2, 3 Erk1, 2, Msk 1, p38, IRS1, PKR, PTEN, CREB, ERa, ERb, DAX, p53, DNMT1, DnMT3B, DnMT3A, TRIP, Rb, MeCP2, Caspase3, La, Furin, EGFP, RFP, Ffluc and Renilla.

In an embodiment of the invention, a composition is provided that includes a mutant RNaseIII containing one or more mutations wherein one mutation is located at a position corresponding to E38 in *E. coli* RNase III in which the glutamic acid (E) has been mutated to an alanine (A). The composition may further include a large dsRNA.

refers to the size of the dsRNA fragments produced by the unmodified enzymes specified in a buffer containing magnesium ions.

Figure 2:
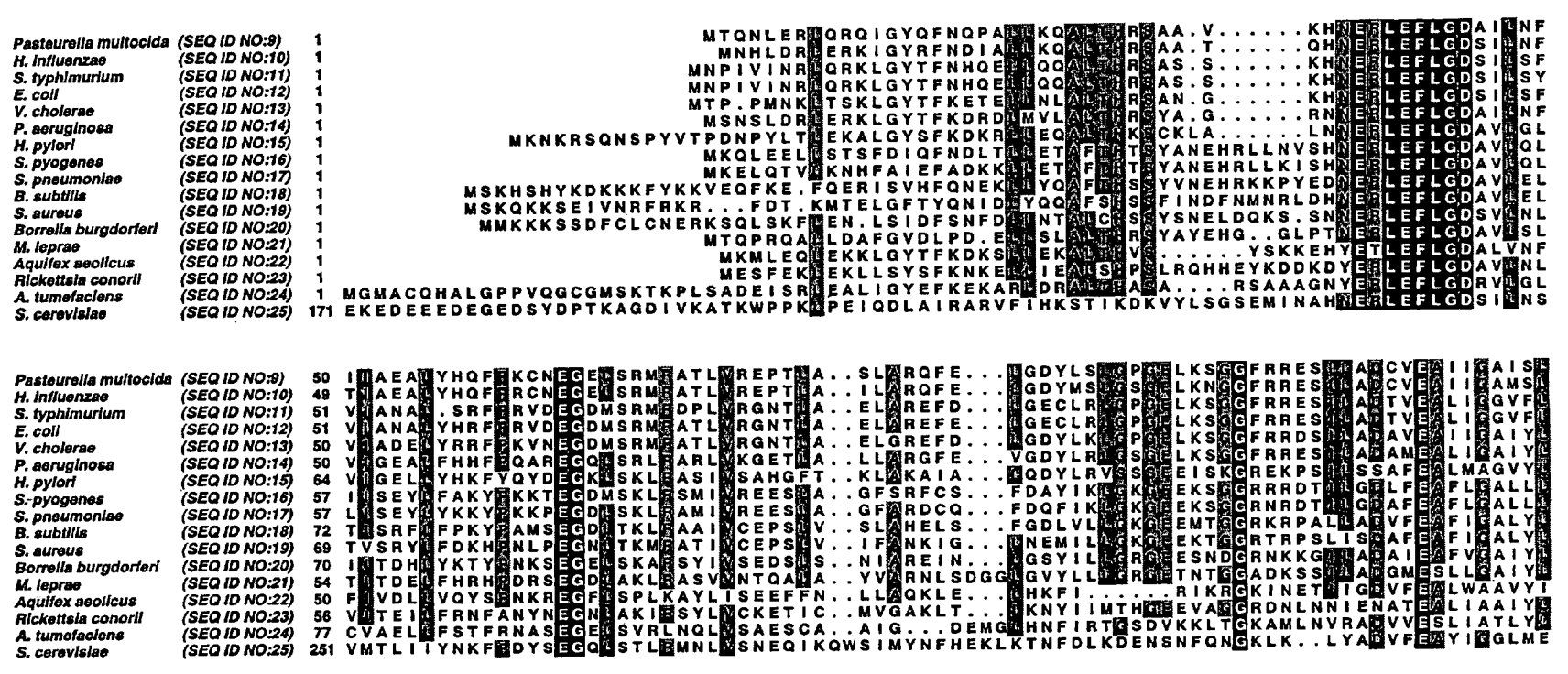

FIG. 2 shows an amino acid alignment of various bacterial and yeast RNAse III enzymes (SEQ ID NOS:9-25) Residues highlighted:

in black—100% conserved among all examples shown;
in gray—conserved among a majority of examples shown;
star—residues proposed to be in contact with dsRNA (Structure 9:1225 (2001)).

Figure 3:
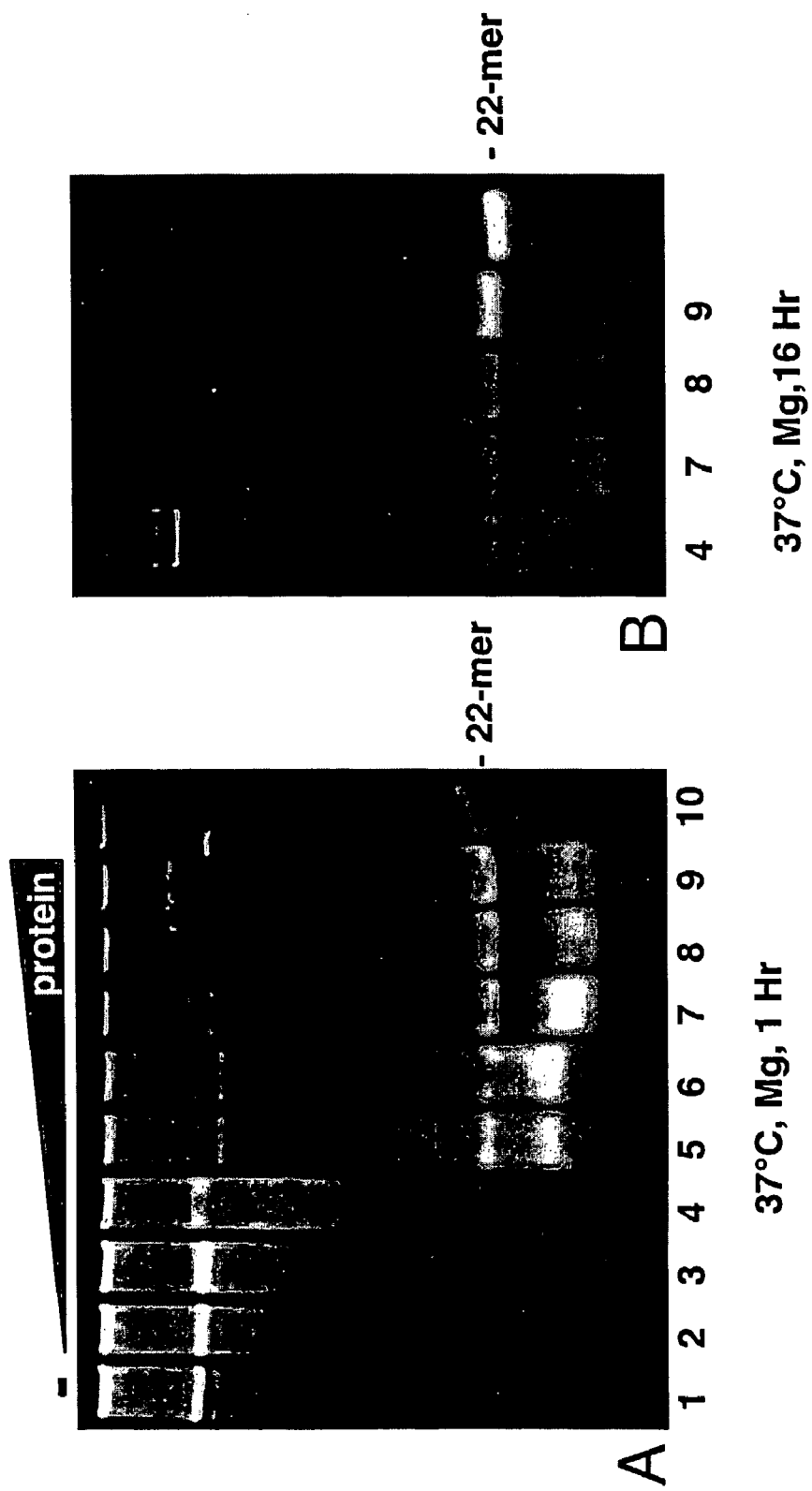

FIG. 3 shows the activity of E38A mutant RNAse III (E38A).

A His-tagged E38A RNAse III fusion was purified by standard Nickel resin affinity purification and protein concentration determined by standard methods. Digestion of 0.5 mg of substrate MalE dsRNA (900 bp) with a serial dilution of E38A mutant RNase III in 50 mM NaCl, 10 mM TRIS HCL, 10 mM MgCl2, 1 mM DTT pH 7.9 (NEB Buffer 2) (New England Biolabs, Inc., Beverly, Mass.) at 37° C., for 1 hr is shown. The reaction mixtures were then electrophoresed through 20% polyacrylamide gel and visualized via staining with Ethidium Bromide.

FIG. 3A: 0.5 µg dsRNA substrate was cleaved with the following amounts of E38A mutant RNAse III: 0.03, 0.06, 0.125, 0.25, 0.5 , 1, 2, and 4 µg (lanes 2-9) for one hour at 37° C. in a volume of 20 µl where 10 µl was loaded in each well.

Lane 1—no enzyme.
Lane 10—synthetic dsRNA 22-mer (size marker).

Lane 7 incubation of 0.5 µg of dsRNA with 1 µg of enzyme resulted in complete digestion. (Complete digestion is here defined as no dsRNA substantially larger than the 22 bp band observed by gel electrophoresis).

Lane 9 shows that the amount of 22 bp product is ~60% of the dsRNA substrate. dsRNA was quantitated by densitometry using known amounts of synthetic dsRNA 22-mer to construct the standard curve.

FIG. 3B: Digestions were set up as in FIG. 3A but were incubated overnight, demonstrating enhanced stability of the approximately 22 bp product over an extended period of time in the presence of the complete RNAse III containing mixture.

Lane numbers correspond to enzyme conditions in FIG. 3A.

Figure 4:
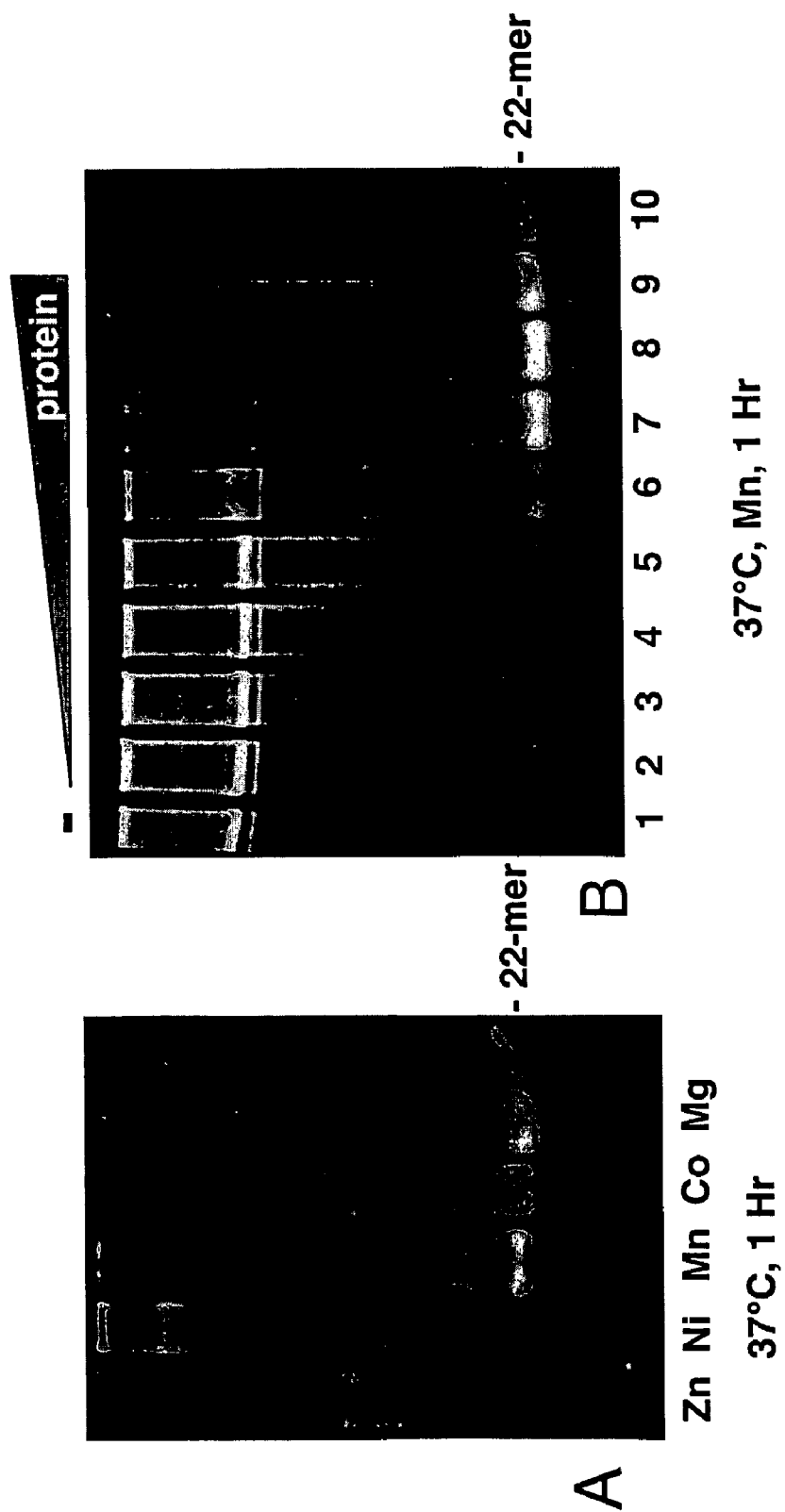

FIG. 4 shows the results of digestion with E38A mutant RNase III under the conditions described for FIG. 3.

FIG. 4A: Digestion of 0.5 µg of dsRNA with 4 µg of mutant RNase III in a volume of 20 µl of buffer containing 10 mM of Zinc, Nickel, Manganese, Cobalt or Magnesium salts.

FIG. 4B: Digestion of 0.5 µg of dsRNA with series of two fold dilutions of the 4 µg mutant RNase III in a volume of 20 µl of buffer containing 10 mM Mn salt:

Lane 1—no enzyme.
Lane 10—synthetic dsRNA 22-mer.

Figure 5:
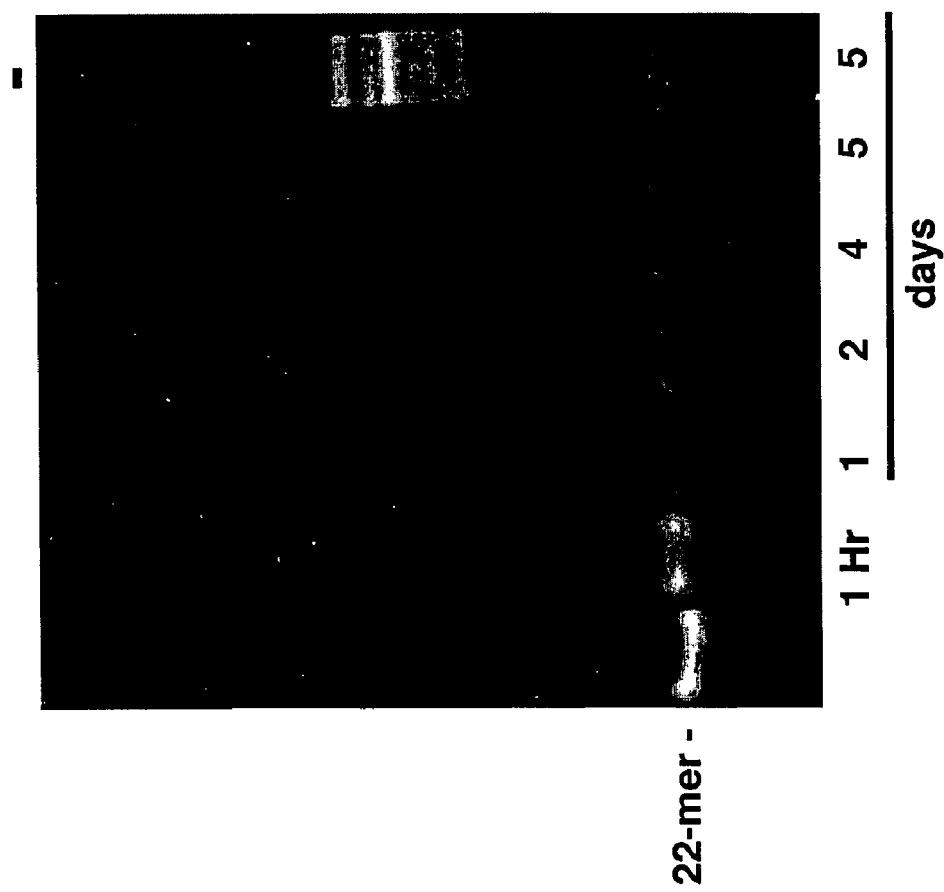

FIG. 5 shows a time course reaction using 4 µg of 900 bp MalE dsRNA and 32 µg of E38A RNAse III in NEB Buffer 2, 160 ml total volume, at 37° C. 10 ml samples were removed at times indicated—1 hour, 1 day, 2 days, 3 days, 4 days and 5 days and reactions stopped by the addition of EDTA to a final concentration of 25 mM.

1st lane on left of gel contains a synthetic 22 bp dsRNA size standard;

Last lane on right of gel contains the product of a 5 day mock-digested dsRNA.

Figure 6:
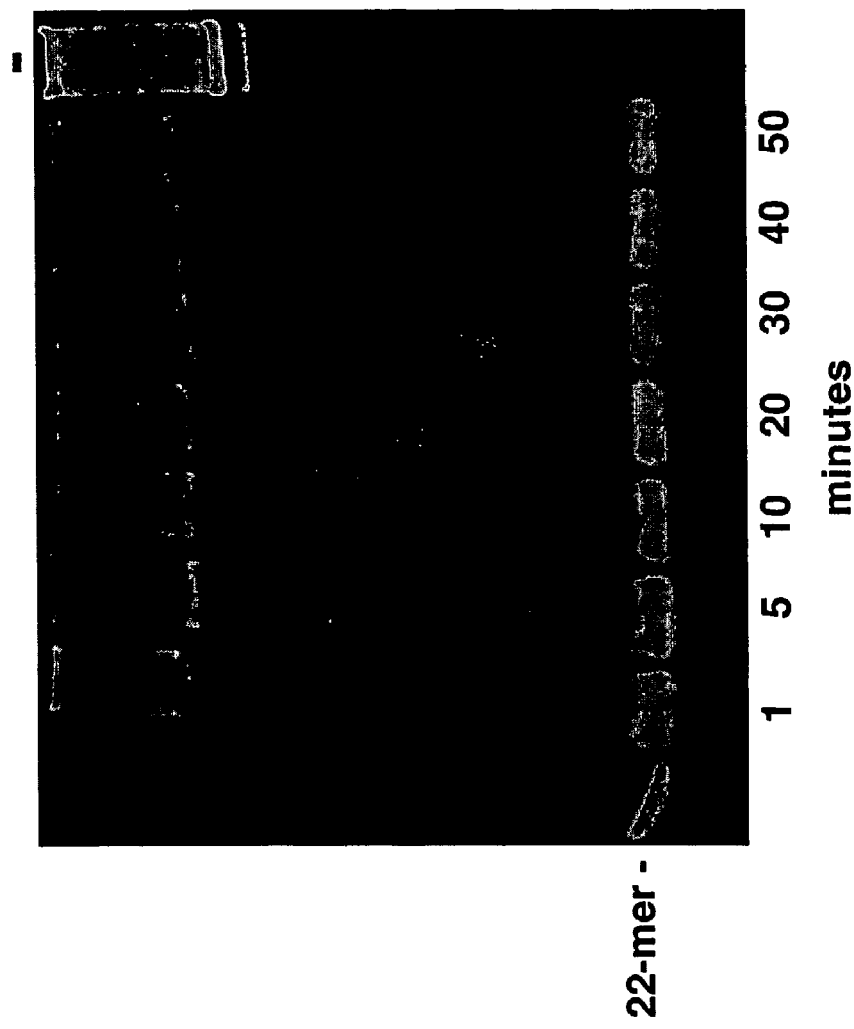

FIG. 6 shows the results of an enzyme reaction performed as described for FIG. 5 for times indicated in minutes.

From left to right: synthetic 22-mer dsRNA size marker; 1, 5, 10, 20, 30, 40 and 50 minute digestions and undigested dsRNA.

Figure 7:
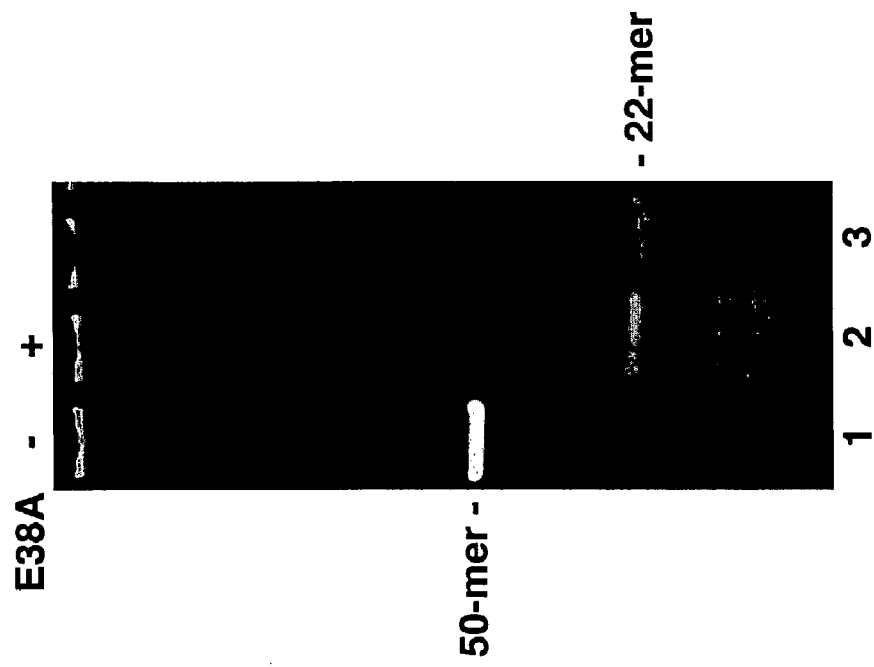

FIG. 7 shows the results of an enzyme reaction performed as described for FIG. 3.

Lane 1, mock digestion of synthetic dsRNA 50-mer;
Lane 2, E38A digestion of synthetic dsRNA 50-mer;
Lane 3, synthetic dsRNA 22-mer.

Figure 8:
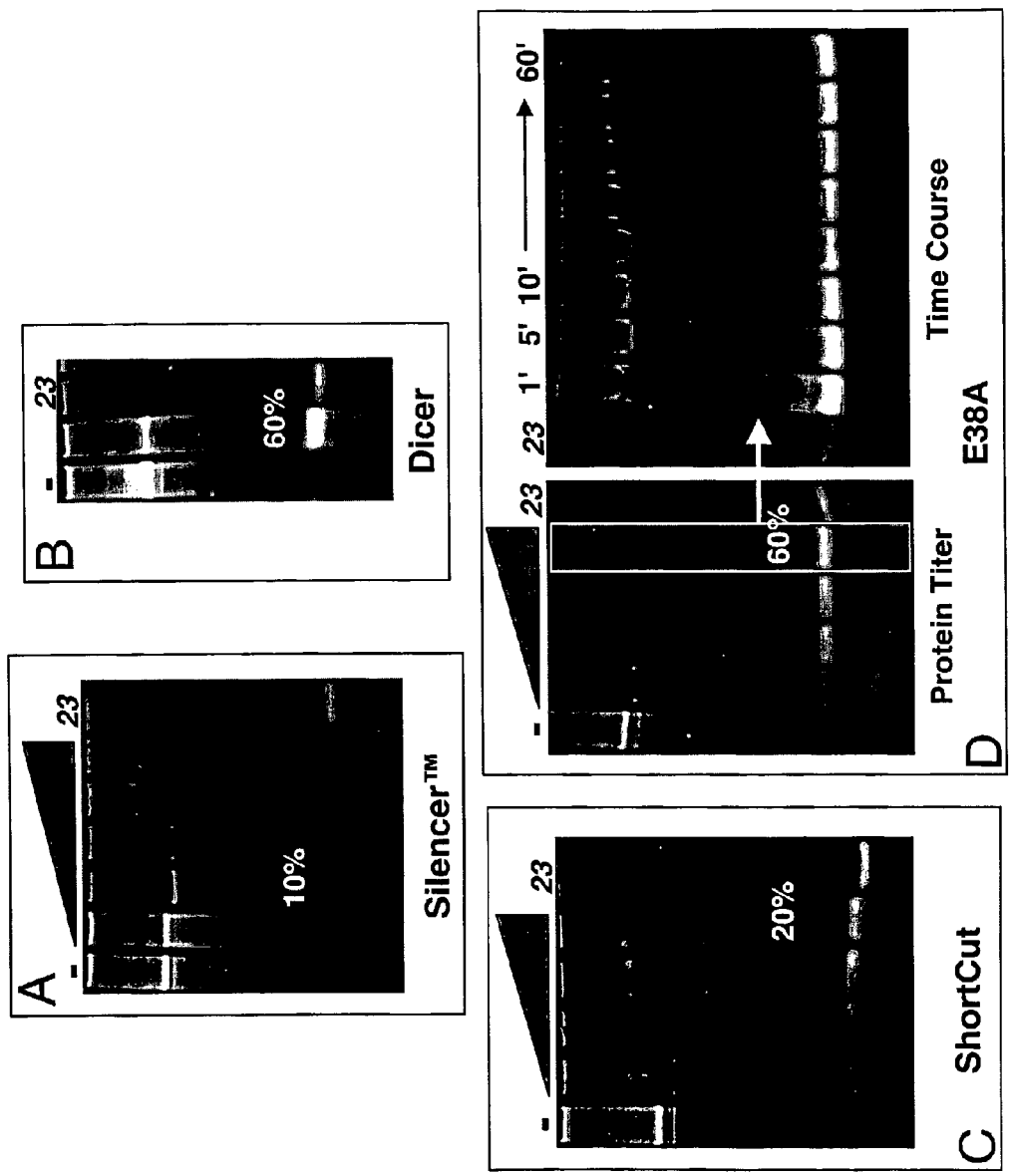

FIG. 8 shows a comparison of different commercial enzyme kits for cleaving dsRNA compared with E38A mutant RNase III. Substrate for each was 0.5 µg of 900 bp MalE dsRNA; conditions for commercial kits are according to manufacturer's instructions. Reaction conditions for E38A are as described for FIG. 3. '-' mock reaction; '23'—synthetic dsRNA 23-mer. Percentiles are product yields for those reaction conditions in lanes indicated. The product yields of dsRNA fragments were quantitated as described for FIG. 3.

FIG. 8A: Silencer™ siRNA Cocktail Kit (RNAse III) (Ambion, Austin, Tex.).

FIG. 8B: Dicer—recombinant dicer (human) (Stratagene, La Jolla, Calif.).

FIG. 8C: ShortCut (RNaseIII)—ShortCut RNAi Kit (New England Biolabs, Inc., Beverly, Mass.).

FIG. 8D: E38A—Left panel shows serial dilution titer starting at 4 µgs (right) and ending in 0.5 µgs (left). Shorter digestions were done using reaction conditions shown in designated lane (boxed) for the following times in minutes— 1, 5, 10, 20, 30, 40, 50, 60.

The comparison shows the digestion products of Dicer and E38A mutant RNase III differ in that a significant portion of large dsRNA has not been cleaved in the Dicer digest whereas for E38A, there is no observable large dsRNA. This difference means that unlike for the Dicer cleavage product, no further separation step is required for the E38A mutant cleavage product for removing large dsRNA prior to transfection of cells.

Figure 9:
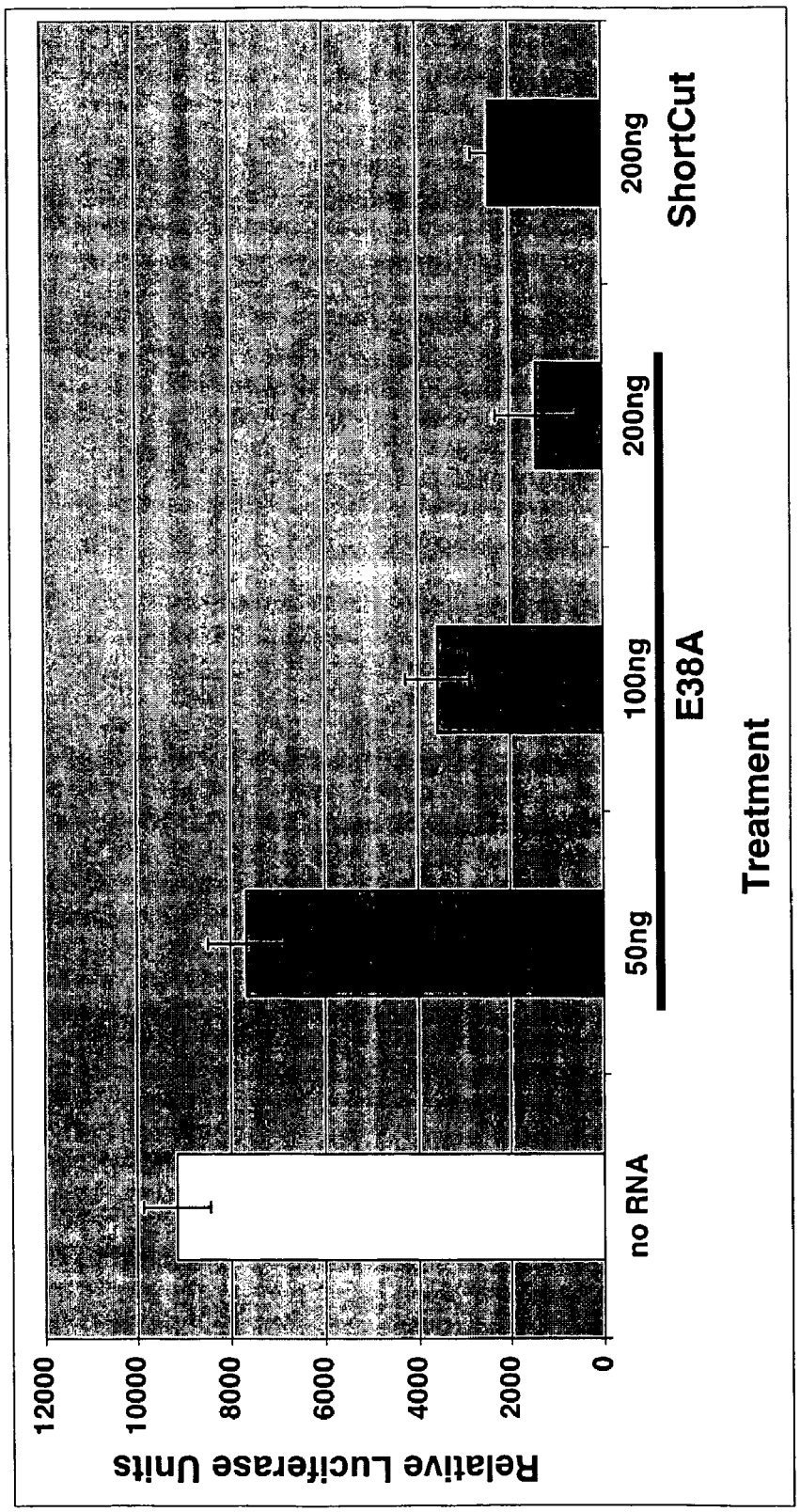

FIG. 9 shows RNA interference activity of Firefly luciferase dsRNA cleaved with either ShortCut RNase III or E38A. Firefly luciferase dsRNA was prepared and digested with either ShortCut RNase III according to manufacturer's instructions, or with E38A according to conditions described for FIG. 3.

NIH 3T3 cells were plated on day one in 24 well plates at 50% density and allowed to grow overnight. Cells were transfected on day 2 with 0.3 mgs per well of a pGL3 vector containing the firefly luciferase gene as a reporter in addition to one containing renilla luciferase as a control using Fugene as the transfection reagent according to manufacturer's instructions. On day 3, luciferase dsRNA prepared by either ShortCut RNAi kit (black bar) or E38A (gray bars) or buffer (white bar) was transfected in the cells. Cells were harvested on day 4 and assayed for luciferase activity using Promega's Dual Luciferase Assay Kit according to manufacturer's instructions (Promega Corporation, Madison, Wis.).

Figure 10:
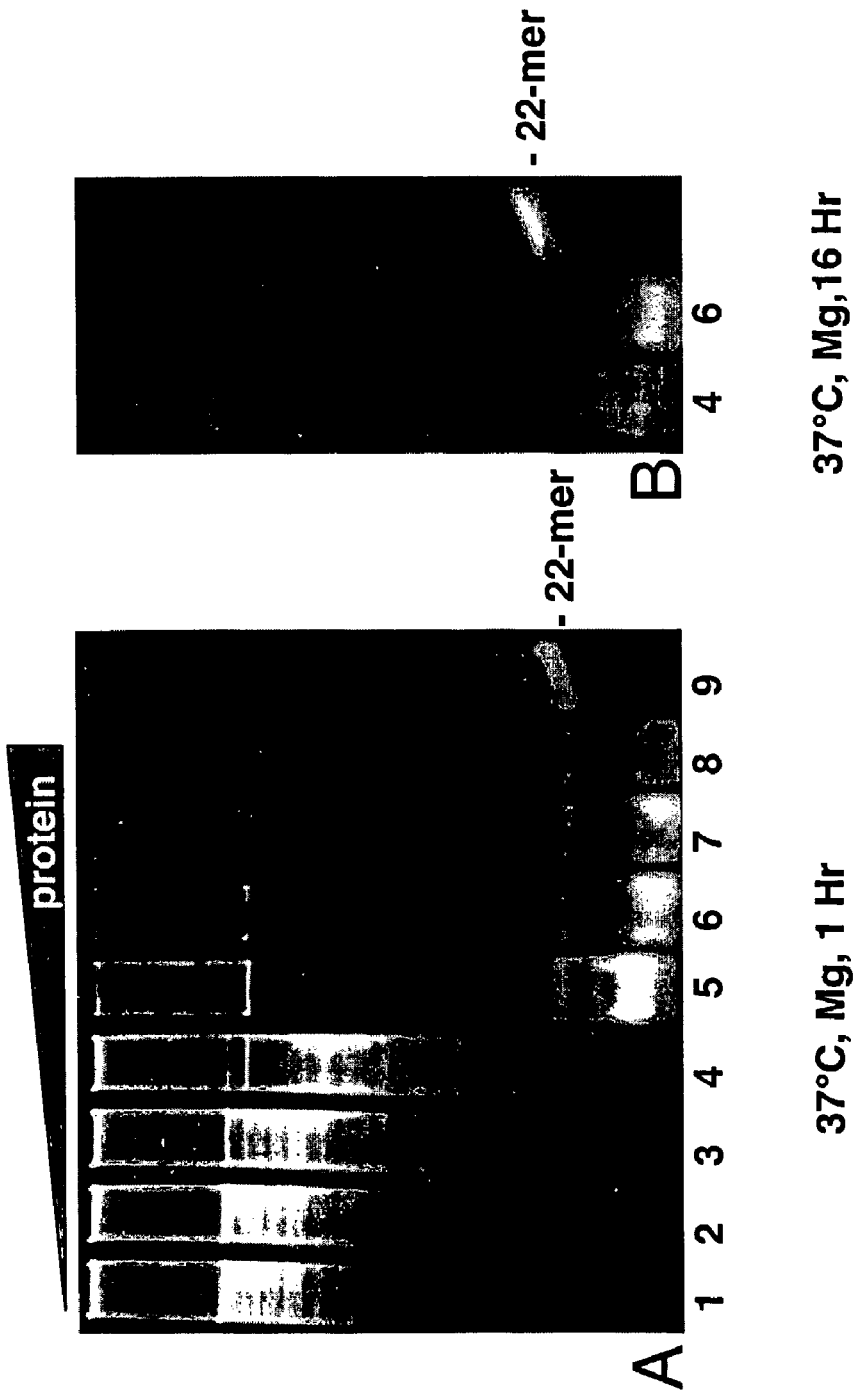

FIG. 10 shows dsRNA cleaved by the E65A mutant RNaseIII. His-Tagged E65A mutation of RNAse III was purified and quantitated as described for FIG. 3.

FIG. 10A: Digestion of 0.5 mgs of MalE dsRNA according to conditions described in FIG. 3 with a serial dilution of E65A mutant RNAse III in NEB Buffer 2 starting a 4 mgs in lane 8 and ending at 32 ngs in lane 1 (New England Biolabs, Inc., Beverly, Mass.).

Lane 9 —synthetic dsRNA 22-mer.

FIG. 10B: Reactions conditions of Lanes 4 and 8 in FIG. 10A were repeated and digestions allowed to go for 16 hours.

Figure 11:
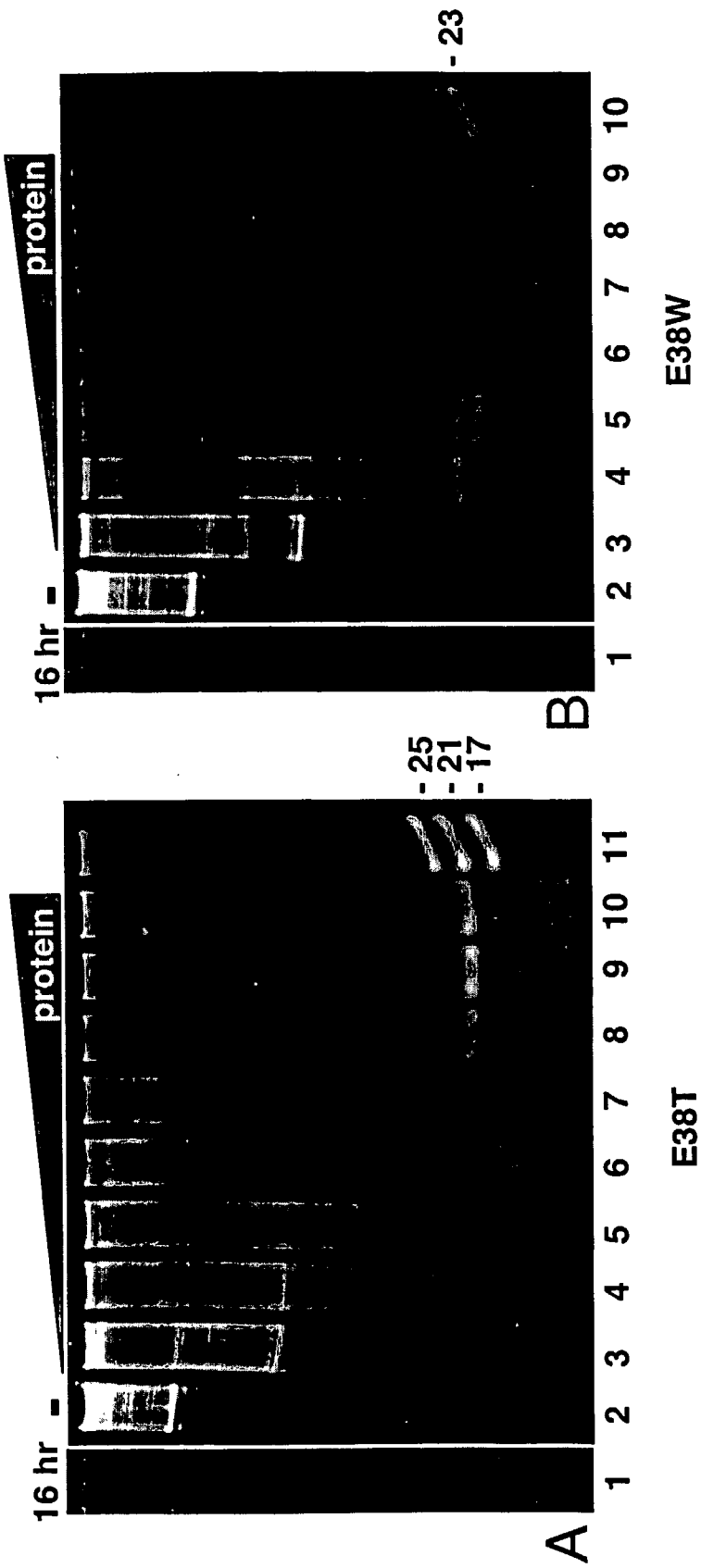

FIG. 11 shows activity of E38T and E38W mutants. His-Tagged E38T and E38W mutations of RNAse III were purified and quantitated as described for FIG. 3.

Digestion of 0.5 μg of MalE dsRNA (900 bp) with serial dilutions of E38T (FIG. 11A) and E38W (FIG. 11B) mutations of RNAse III in NEB Buffer 2 at two fold dilutions of 4 μg of mutant enzyme starting in lane 10 (FIG. 11A) and lane 9 (FIG. 11B) (New England Biolabs, Inc., Beverly, Mass.). Digestions were conducted at 37° C. for 30 minutes. Mock digestions are shown in lane 2 (FIGS. 11A and 11B) and overnight digestions using 4 μg of each mutant shown in lane 1 (FIG. 11A and 11B). dsRNA size standards are in lane 11 (FIG. 11A) and lane 10 (FIG. 11B).

FIG. 12 shows an alignment of RNase III from *Aquifex aeolicus* and *E. coli* highlighting regions and specific amino acids of the protein thought to interact with dsRNA and be involved with cutting of the dsRNA (Blaszczyk, J., et al. Structure 9:1225 (2001)). Numbers indicate residue number of the amino acid to its right. Top row shows sequence of RNase III from *A. aeolicus*; second row shows sequence of wt RNase III from *E. coli*. All rows below show sequences of *E. coli* RNase III mutants which were assayed for activity. Mutant designations are listed in Column 1. Activity of each mutant listed in Column 2—wt—wild type activity, 23—activity produces dsRNA fragments of about 23 nt. i—inactive mutant residues are boxed and highlighted; gray, inactive; black, producing 23-mer dsRNA; no highlight, wild type. *E. coli* residues: 38, 45, 65, 117 correspond to *A. aeolicus* residues 37, 44, 64, 110, respectively.

Figure 13:
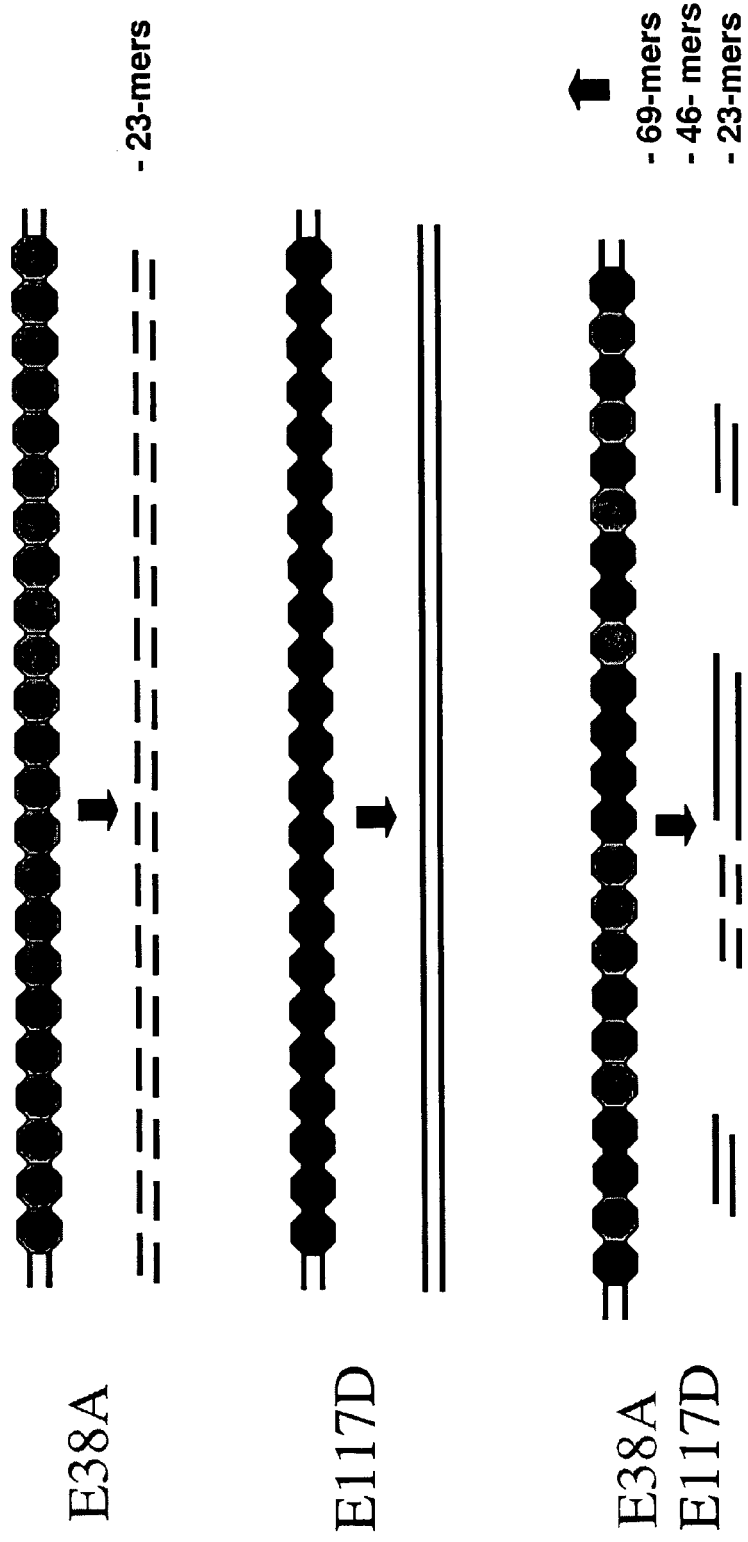

FIG. 13 shows a cartoon depiction of activity of RNAse III E38A and E117D. Top panel—E38A (gray hexagons) binds dsRNA (parallel lines) and cleaves it yielding a dsRNA 23-mer. Middle panel—E117D (black hexagons) binds dsRNA and does not cleave. Bottom panel—proposed result from mixing E38A and E117D in one reaction. The dsRNA would be cleaved yielding a dsRNA ladder composed of multimers of the 23-mer product of E38A alone. The size ladder can be shifted up or down by varying the ratios of the two mutants.

Figure 14:
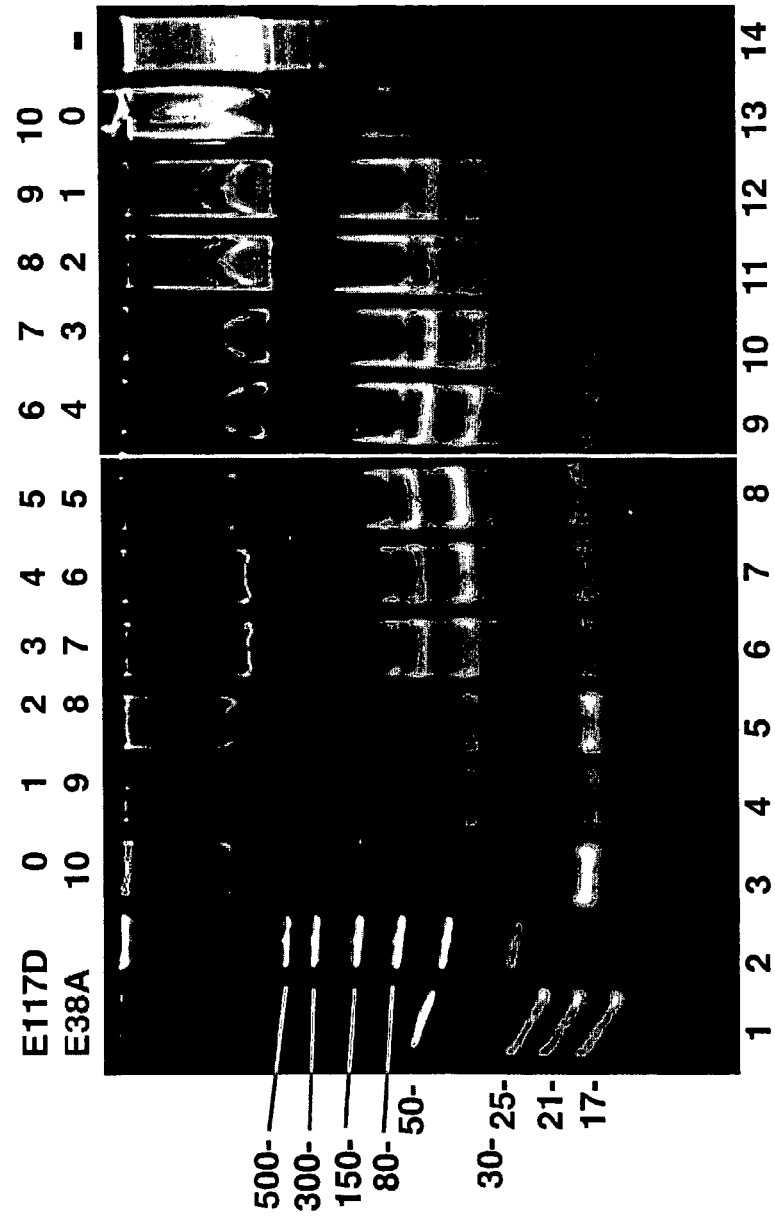

FIG. 14 shows an E38A/E117D mixing experiment. E38A and E117D were mixed in varying ratios, placed on ice then used in dsRNA digestions under conditions described in FIG. 3, 4 mgs of total enzyme was mixed with 0.5 μg of dsRNA. Lane 1, 2—dsRNA size standards, sizes shown; Lanes 3-13, digestions using ratios shown on top of gel; Lane 14—mock digestion.

Figure 15:
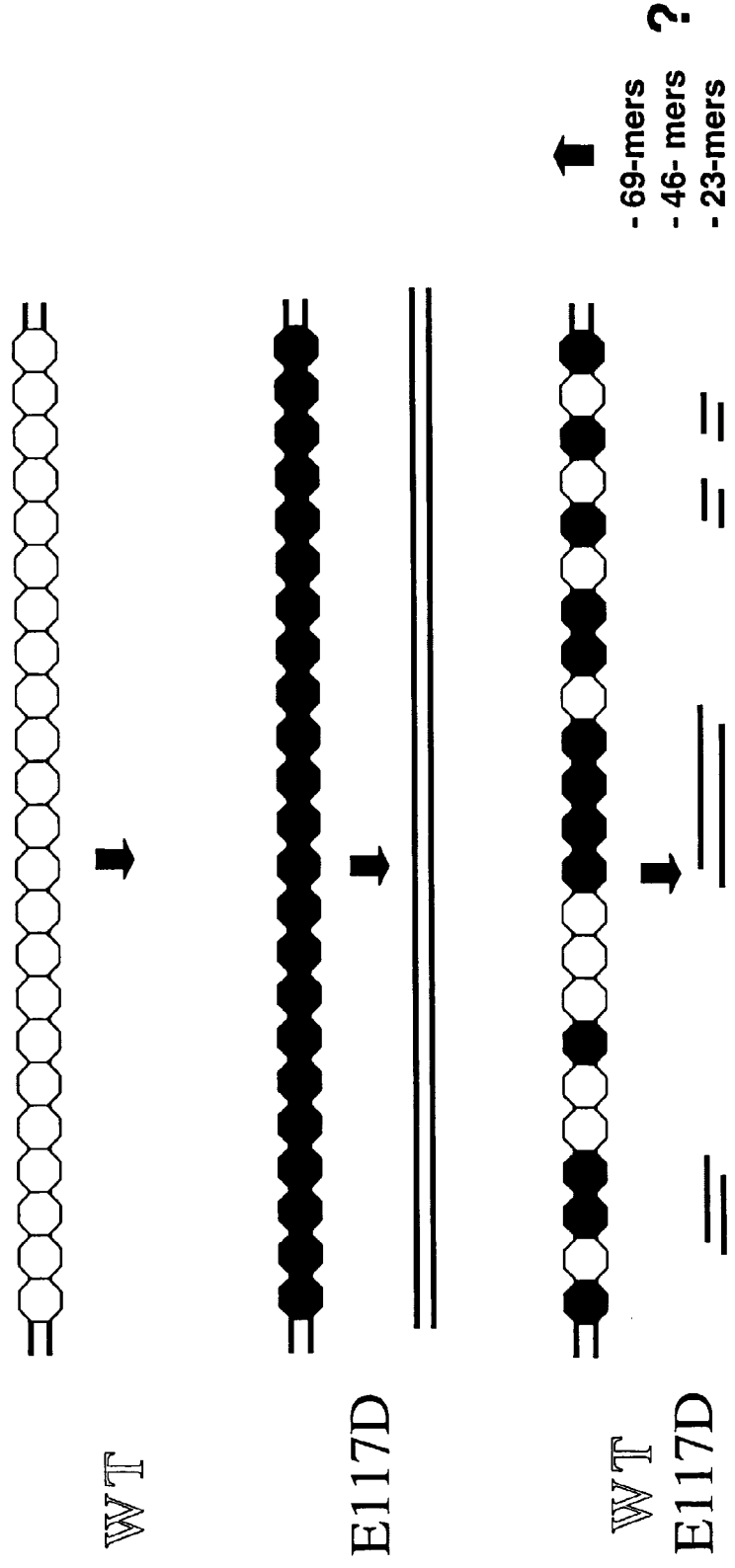

FIG. 15 shows a cartoon depicting activity of RNAse III WT and E117D. Top panel—WT (white hexagons) binds dsRNA (parallel lines) and cleaves it yielding a dsRNA 11-mer or smaller. Middle panel—E117D (black hexagons) binds dsRNA and does not cleave. Bottom panel—proposed result from mixing WT and E117D in one reaction. The dsRNA would be cleaved yielding two sets of products: 11-mers or smaller products that would not be seen on a gel, and a dsRNA ladder composed of multimers of the 23-mer product resulting from E38A mutant RNaseIII digestion alone. The size ladder can be shifted up or down by varying the ratios of the two mutants.

Figure 16:
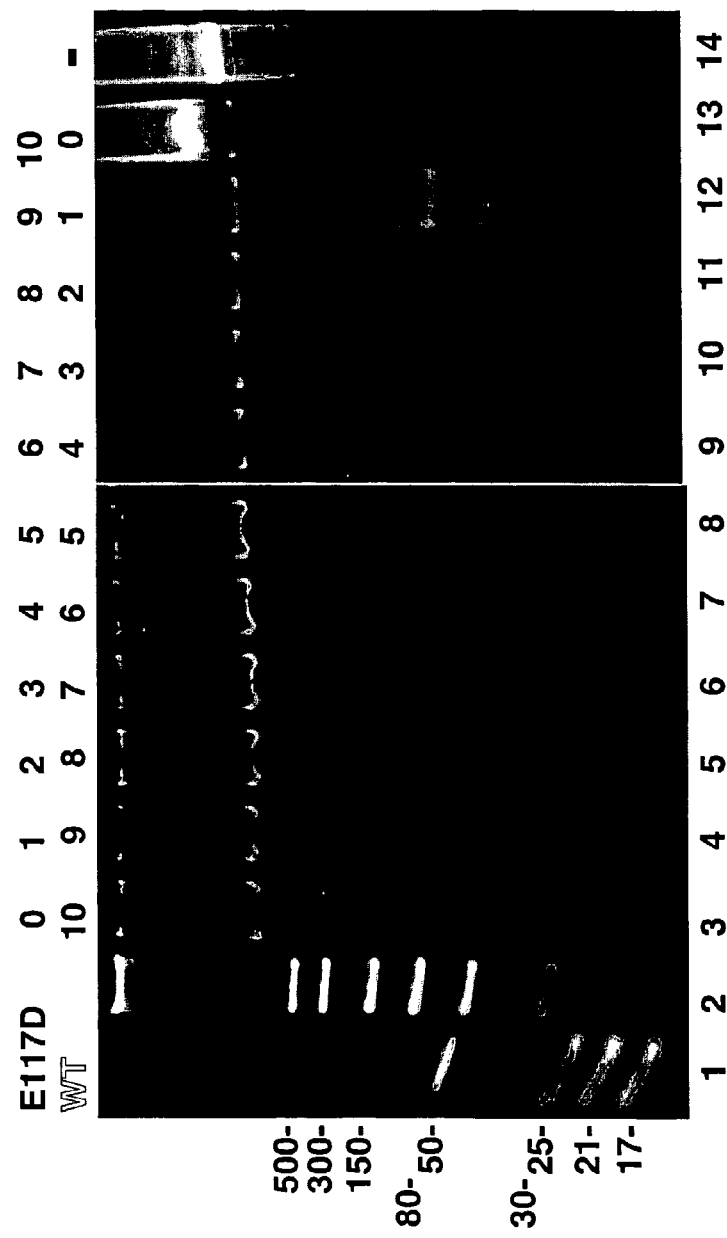

FIG. 16 shows a WT RNaseIII mixed with the mutant E117D in a mixing experiment. WT and E117D were mixed in varying ratios, placed on ice then used in dsRNA digestions under conditions described in FIG. 3. 4 mgs of total enzyme was mixed with 0.5 mg of dsRNA. Lane 1, 2—dsRNA size standards, sizes shown; Lanes 3-13, digestions using ratios shown on top of gel; Lane 14—mock digestion.

Figure 17:
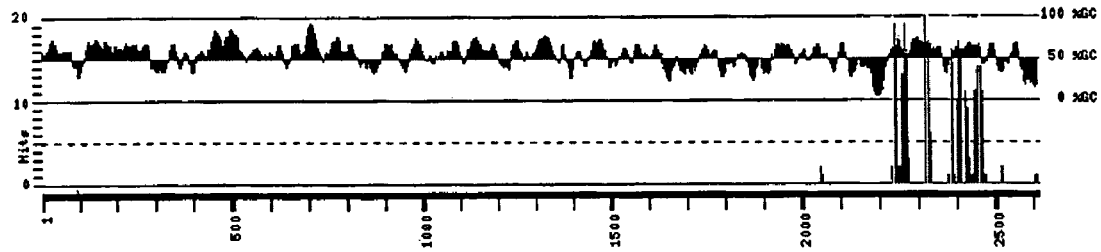

FIG. 17 shows output for human P53 sequence analyzed according to the algorithm in Example VI.

DESCRIPTION OF THE EMBODIMENTS

We report the selective generation of dsRNA fragments suitable for effective silencing of gene expression by means of digestions with RNase III mutants in the presence of standard buffers containing magnesium ions (FIGS. 3-11) or manganese ions. Different types of mutants are described including: single point mutations altering RNA binding or cleavage residues and double point mutants. Examples of mutants are provided in the figures (FIG. 12) and examples (see, for example, Example 1) that have comparable or improved activity to that described for wild type RNase III in a manganese-containing buffer (US published application US-2004-0038278).

The mutant RNase IIIs can be produced recombinantly with a high yield. These enzymes are convenient to use for reasons that include: the time of incubation of enzyme with substrate is not critical and the enzyme does not need to be titrated to determine a specific concentration for each use. These features make the mutant RNase III especially useful for high through-put reactions. The dsRNA product obtained after mutant RNaseIII digestion has been shown here to be effective in gene silencing.

It has been demonstrated here that mixing a wild type or active mutant RNase III with an inactive mutant (E117D) can result in the formation of nucleic acid size ladders as demonstrated in FIGS. 13 to 16. In FIG. 13, E38A mutant RNaseIII and E117D are reacted with template DNA to produce products of varying size. This is because E117D binds to template but does not cleave the substrate so as to block potential cleavage sites for E38A. This effect is demonstrated in FIG. 14. Similarly, wild type RNaseIII and E117D are mixed together, a ladder of different sized fragments are observed (FIG. 16).

The following terms as used in the description and in any accompanying claims have been defined below. These definitions should be applied unless the context in which the terms are used requires otherwise.

"hsiRNA mixture" refers to a heterogeneous (h) mixture of short double-stranded RNA fragments containing at least one fragment (siRNA) suitable for silencing gene expression. The RNA fragments in the hsiRNA mixture consistently contain a substantial fraction (greater than about 15% of the total number of fragments) having a length of 18-25 base pairs as determined by ethidium-stained native polyacrylamide gel analysis. The presence of fragments larger than 25 nucleotides or smaller than 18 nt is not excluded. The hsiRNA mixture is preferably obtained by digesting "large" dsRNA with a mutant RNAseIII.

"Silencing" refers to partial or complete loss-of-function through targeted inhibition of gene expression in a cell and may also be referred to as "knock down". Depending on the circumstances and the biological problem to be addressed, it may be preferable to partially reduce gene expression. Alternatively, it might be desirable to reduce gene expression as much as possible. The extent of silencing may be determined by any method known in the art, some of which are summarized in International Publication No. WO 99/32619 incorporated herein by reference. Depending on the assay, quantitation of gene expression permits detection of various amounts of inhibition, for example, greater than 10%, 33%, 50%, 90%, 95% or 99%.

"Large double-stranded RNA" refers to any dsRNA or hairpin having a double-stranded region greater than about 40 base pairs (bp) for example, larger than 100 bp or more particularly larger than 300 bp. The sequence of a large dsRNA may represent one or more segments of one or more mRNAs or the entire mRNAs. The maximum size of the large dsRNA is not limited herein. The dsRNA may include modified bases where the modification may be to the phosphate sugar backbone or to the nucleotide. Such modifications may include a nitrogen or sulfur heteroatom or any other modification known in the art. The dsRNA may be made enzymatically, by recombinant techniques and/or by chemical synthesis or using commercial kits such as MEGASCRIPT® (Ambion, Austin, Tex.) and methods known in the art. An embodiment of the invention utilizes HiScribe™ (New England Biolabs, Inc., Beverly, Mass.) for making large dsRNA. Other methods for making and storing large dsRNA are described in International Publication No. WO 99/32619.

The double-stranded structure may be formed by self-complementary RNA strand such as occurs for a hairpin or a micro RNA or by annealing of two distinct complementary RNA strands.

"Heterogeneous" in the context of an hsiRNA mixture refers to dsRNA fragments having non-identical sequences produced from a single large dsRNA or a mixture of large dsRNAs after cleavage with RNase III or mutants thereof. The fragments collectively contain sequences from the entire length of the large RNA and hence form a heterogeneous mixture.

Figure 1:
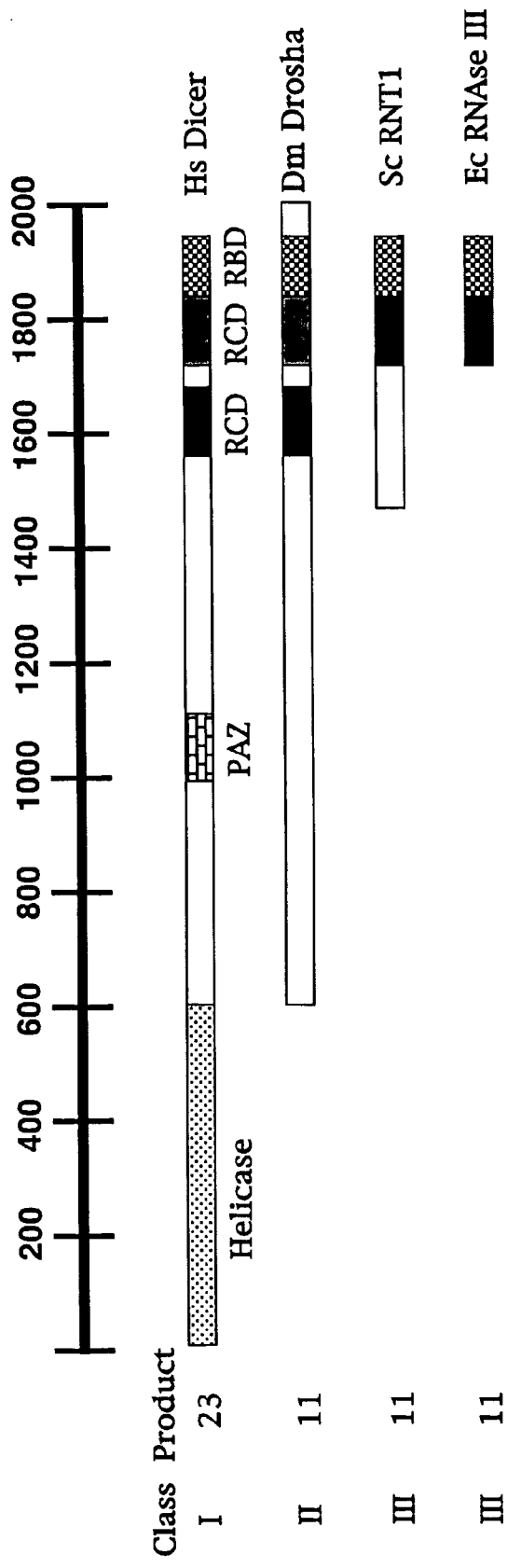
FIG. 1 shows a cartoon of an alignment of examples of the 3 classes of RNAse III enzymes—human dicer (Hs Dicer); Drosophila Drosha, (Dm Drosha); S. cerevisiae RNAse III (Sc RNT1); *E. coli* RNAse III (Ec RNAse III). Top line—amino acid residue numbers. Class designations as I, II and III with corresponding dsRNA product size in base pairs. Protein domains designated as follows: helicase, stippled; PAZ, brick; RNA binding domain (RBD), checkered; RNA cleavage domain (RCD), black; RNA cleavage domain with one or more substitutions at homologous residues, grey. "Product"

"RNase III" refers to a naturally occurring enzyme or its recombinant form. The RNase III family of dsRNA-specific endonucleases is characterized by the presence of a highly conserved 9 amino acid stretch in their catalytic center known as the RNase III signature motif (see below). Mutants and derivatives are included in the definition. The utility of bacterial RNase III described herein to achieve silencing in mammalian cells further supports the use of RNases from eukaryotes, prokaryotes viruses or archea in the present embodiments based on the presence of common characteristic consensus sequences. Embodiments of the invention do not preclude the use of more than one RNase to prepare an RNA fragment mixture. Any RNase can be used herein where the RNase contains the amino acid consensus sequence [DEQ][KRQT][LM]E[FYW][LV]GD[SARH] (PROSITE: PDOC00448 documentation for the RNase III). While not wishing to be bound by theory, it is here suggested that there is a region in an RNAse III of this type that specifically contacts substrate RNA. This region includes 4 specific amino acids and it is here shown that a mutation in at least one particular amino acid of this region results in increased activity of the RNase III for purposes of producing dsRNA fragments. FIG. 1 shows characteristic functionalities of RNases, FIG. 2 shows conserved sequences in RNases from different sources and FIG. 12 shows a variety of mutations in different regions of the RNase III tested by applicants.

The designation for the mutants are assigned by an amino acid position in a particular RNase III isolate. These amino acid positions may vary between RNase III enzymes from different sources. For example, E38 in *E. coli* corresponds to E37 in *Aquifex aeolicus*. The position E38 in *E. coli* and E37 in *A. aeolicus* correspond to the first amino acid position of the consensus sequence described above and determined by aligning RNase III amino acid sequences from the public databases by their consensus sequences. Embodiments of the invention are not intended to be limited to the actual number designation. Preferred embodiments refer to relative position of the amino acid in the RNase III consensus sequence.

Mutations in the RNAse III refer to any of point mutations, additions, deletions (though preferably not in the cleavage domain), rearrangements (preferably not in the domain linking regions). Mutations may be at a single site or at multiple sites in the RNase III protein. Mutations can be generated by standard techniques including random mutagenesis and targeted genetics. Example 1 gives one approach to making mutants but this approach is not intended to be limiting.

Examples of mutants include E38A, E38T, E38W and E65A which produced a 23 bp product. E65A, E38T, E38W as determined by gel electrophoresis differed from E38A with respect to stability in a 16 hour incubation (see FIG. 11) but were at least as effective as wild type RNase III in generating dsRNA fragments. E38A, E38T, E38W and E65A mutants produced an increased yield of the 23 bp product as compared to wild type RNase III in $Mg^{2+}$ buffer. While not wishing to be bound by theory, it is postulated here that E38A binds and cleaves dsRNA template and is not then readily disassociated from the dsRNA product. The complex appears to be relatively stable and the dsRNA product is not available for further cleavage by RNase III, wt or mutant. This may explain why mutant RNase III digestion can be performed overnight without causing the entire sample to be cleaved to small fragments such as 11 nt fragments.

"Complete digestion" refers to an RNaseIII reaction in which fragments of dsRNA of a size greater than about 30 base pairs (excluding digested material retained in the loading well or bound to enzyme) are at such low concentration that are they are not readily detected on an ethidium bromide stained 20% polyacrylamide gel.

"Host cell" refers to cultured eukaryotic cells or cells in animals, including vertebrates such as mammals including humans, and invertebrates such as insects. Host cell also refers to cells from plants and microorganisms.

"Overlapping" refers to when two RNA fragments have sequences which overlap by a plurality of nucleotides on one strand, for example, where the plurality of nucleotides (nt) numbers as few as 2-5 nucleotides or by 5-10 nucleotides or more.

"Complementary sequence" refers to a sequence which is not necessarily 100% identical to a sequence to which it hybridizes but nevertheless is capable of hybridizing to a specified nucleic acid under stringent conditions where stringent conditions may include: 400 mM NaCl, 40 mM PIPES pH 6.4, 1 mM EDTA, 50° C. or 70° C. for 12-16 hours followed by washing. Sequence variations can be tolerated such as those that arise due to genetic mutation, strain polymorphism, evolutionary divergence or chemical modifications.

"Part or all" of a messenger RNA refers to that part of the messenger RNA (mRNA) which is complementary to a large dsRNA.

"Substantial portion" refers to the amount of sequence of a large dsRNA represented in sequences contained in an hsiRNA mixture. In one embodiment, the representative sequence is greater than 20%. In other embodiments, the representative sequence may be greater than 30%, 40%, 50%, 60%, 70%, 80% or 90%.

"One or more dsRNAs" refers to dsRNAs that differ from each other on the basis of sequence.

"Target gene or mRNA" refers to any gene or mRNA of interest. Indeed any of the genes previously identified by genetics or by sequencing may represent a target. Target genes or mRNA may include developmental genes and regulatory genes as well as metabolic or structural genes or genes encoding enzymes. The target gene may be expressed in those cells in which a phenotype is being investigated or in an organism in a manner that directly or indirectly impacts a phenotypic characteristic. The target gene may be endogenous or exogenous. Such cells include any cell in the body of an adult or embryonic animal or plant including gamete or any isolated cell such as occurs in an immortal cell line or primary cell culture.

The term "stable preparation" is used here and in the claims to describe a preparation of template dsRNA which is cleaved in the presence of a mutant RNaseIII where at least 30% of the starting material is cleaved into fragments having a size of about 18-30 nt more particularly about 21-23 nt and the cleavage product is stable for more than 2 hours, more particularly stable for 5 hours more particularly stable for 16 hours. Stability relates to the absence of detectable change in the size profile and amount of RNAse III reaction product on a gel at a specified time. Stability may be a relative measure observed by comparing mutant to wild type RNAse III reaaction products The introduction of an hsiRNA mixture into vertebrate, invertebrate, plant or protoplast cells, or micro-organisms may be achieved directly into the cell or introduced extracellularly into a cavity or interstitial space, into the circulation of an organism, orally, by bathing, transdermally, by a transmucosal route, topically or by use of viral vectors to infect the host with the DNA.

Standard protocols of transfection or transformation may be used for introducing dsRNA into cells in culture, for example, protocols using transfection reagents in the NEB catalog (New England Biolabs, Inc., Beverly, Mass.) or Lipofectamine 2000, Oligofectamine (Invitrogen, Carlsbad, Calif.), TRANS-IT TKO® (Mirus Corp., Madison, Wis.), Targefect (Targeting Systems, Santee, Calif.), calcium phosphate or electroporation. Engineered vectors containing fragments from hsiRNA or siRNA can include bacterial vectors, plasmids or viral vectors for transforming or transfecting whole organisms. A gene gun may be utilized for plants for directing dsRNA into chloroplasts for example. The methodology for introducing foreign nucleic acids into organisms and cells is well known in the art. Introduction of the dsRNA mixture via DNA clones expressing individual fragments from a particular dsRNA mixture into whole animals can be achieved by means of standard techniques for introducing nucleic acids.

In this specification and the appended claims, "a", "an" and "the" is not intended to be limited to a single form unless the context clearly dictates otherwise.

Advantages of the methods described herein include:

(a) obtaining rapidly (within minutes) an enhanced concentration of dsRNA fragments of a size suitable for silencing of gene expression by a rapid, cost effective process that is not dependent on a further size separation step. The methodology provides dsRNA fragment preparations from large dsRNA that contain a plurality of overlapping dsRNA fragments in which less than about 20% are uncut large dsRNA and more about 30% have a fragment size of 18-30 base pairs more particularly 21-23 bp. In preferred embodiments of the method, as much as 60% of the large dsRNA is cleaved into fragments of 21-23 nt. Because of its simplicity, this approach is amenable to automation and high throughput;

(b) forming a preparation of dsRNA fragments with gene silencing activity without requiring identification of the particular fragment giving rise to the gene silencing effect where the preparation is substantially stable without further purification for an extended period of time relative to existing enzymatic approaches;

(c) providing a means to utilize the products of the method by cloning individual fragments or forming libraries or arrays of clones to enable mapping these fragments with respect to the RNA from which they are derived as well as testing individual fragments for gene silencing activity where the libraries may span the entire genome if required; and for in vivo use to provide a continuous supply of siRNA. For example, the siRNA can be incorporated in a plasmid or in a viral vector RNA viruses such as lentiviruses provide a means of infecting cells as well as a cloning vehicle.

(d) providing dsRNA reagents for applications which include: silencing single genes or families of genes in a eukaryotic cell or organism to study function using standard transfection or transformation techniques for nucleic acids;

(e) reduction of off-target effects compared with synthetic dsRNA preparations by, for example, selecting large dsRNA constructs that are designed to be uniquely representative of the target gene with as little homology as possible to other areas of the genome;

(f) using these dsRNA fragments as therapeutic agents or in therapeutic agent screening or target validation assays; and (g) cloning DNA encoding dsRNA fragments to provide a continuous or in vivo regulated supply of gene silencing dsRNA without the need for de novo synthesis for each experiment. Alternatively, the siRNA can be incorporated into the genome of an RNA virus, for example, the lentivirus, for delivery into the host cell.

Other advantages of RNase III mutants such as E38A described herein further include: (i) the ability to obtain the desirable size range of dsRNA products generated by substantially complete digestion of larger dsRNA molecules corresponding to a large portion or the total sequence of the target mRNA so as to circumvent the need for selecting an effective target short sequence; (ii) incubation in standard buffers to facilitate making dsRNA and cleaving it to the desired size all in a single reaction vessel; (iii) enhanced yield relative to wild type RNase III of fragments in the desired size range; (iv) enhanced stability of the fragments obtained using mutant enzymes compared with wild type RNase III in a standard Magnesium buffer; (v) flexibility in time of incubation where a complete reaction can be achieved in as little as 10 minutes although longer incubation times at least up to 16 hours are not detrimental to obtaining the desired reaction products; (vi) reduced cost of gene silencing reagents relative to synthetic products; (vii) opportunities for multiplexing reactions and for generating libraries of fragments; (vii) the ability to form multiple randomly cleaved fragments of dsRNA of about 23 bp from fragments having a size as small as about 50 bps; and (viii) the ability to generate fragments of about 23 bp from large dsRNA in vivo (cell culture or whole organism) by introducing mutant RNase III by transfection, infection or injection using standard protocols.

The fragmentation of large dsRNA molecules (greater than about 40 bp to at least 10 kb) including linear dsRNA or hairpins, provides a population of short RNAs which include multiple effective short sequences (18-30 bp) corresponding to the mRNA for silencing.

Additionally, the advantages of the method described herein obviate the need for calibration of the time of digestion or the amount of enzyme used (FIGS. 2, 3, 4 and 6) beyond a threshhold value where the threshhold of time is a few minutes and the threshhold of concentration may include a range of 1:1 (w/w) of enzyme:substrate. An optional additional step of removing undesired digestion products by gel electrophoresis or other tedious separation methods can be omitted making the method amenable to automation and suitable for high throughput formats. The RNA starting material can be readily obtained by in vitro enzymatic transcription (NEB catalog, New England Biolabs, Inc., Beverly, Mass.) or chemical synthesis and can be a double-stranded molecule or a single stranded RNA that forms a double stranded hairpin.

A fraction of the starting material (large dsRNA), for example, at least 30%, more particularly, greater than 40% or 50%, has a size after digestion with mutant RNase III, in the range of 18-30 bp, more particularly, 21-23 bp suitable for gene silencing in cultured mammalian and insect cells. It is expected that these fragments will also be active in gene silencing in whole organisms such as, plants, microorganisms and animals including humans as well as to cultured cells from the same. Unlike with Dicer, the fragments having a size outside the range of 21-23 nt do not interfere with gene silencing.

In a preferred embodiment, a E38A mutant of RNase III is capable of converting as much as 60% of the substrate to the preferred size range within 10 minutes at 37° C. in standard buffer (NEB buffer 2, New England Biolabs, Inc., Beverly, Mass.). The yield of RNA fragments from digestion of large dsRNA with RNase III E38A mutant may result for example in as much as 2× the yield obtained with RNase III (wt) in the presence of manganese ions and about 10× the yield obtained with RNase III (wt) in the presence of magnesium ions (see, for example, FIG. 7).

One of the problems in the field of gene silencing is that of identifying a short dsRNA (15-30 bp) that can achieve the desired goal of effectively targeting a particular messenger RNA, other RNA or gene. In embodiments of the invention, this problem is solved by utilizing a large dsRNA having a sequence that is identical to all or part of the target and cleaving this large RNA into multiple overlapping fragments of the appropriate size for gene silencing. The selection of a suitable sequence for a dsRNA prior to cleavage can be determined for example by the algorithm in Example VI. It is here asserted that the cleavage products are representative of the entire length of the large dsRNA and that the dsRNA fragment preparation is capable of gene silencing in a variety of cells including insect cells and mammalian cells. Importantly, off-target effects are minimized by the use of hsiRNA mixtures.

Once a dsRNA fragment mixture is obtained, it is possible to make a library of clones containing DNA sequences corresponding to individual dsRNA fragments in the mixture. When provided with appropriate promoters, individual clones or mixtures thereof can be used to transfect cells so as to provide a continuous supply of the short dsRNA for use in long-term gene silencing. Silencing of gene expression as a result of transfection of an individual clone or selected mixtures of clones into a target cell or organism may have particular advantages in for example, therapeutic applications, over transient gene silencing effects achieved by transfecting cells with the dsRNA itself. This provides new reagents for therapeutic applications providing an unlimited supply of an agent that specifically modulates gene expression of a particular gene.

Specificity of Gene Silencing

Specificity of gene silencing for a particular targeted mRNA can be confirmed using a BLAST analysis of sequences in the targeted mRNA to determine that no extended regions in the RNA (over 11 bases long) are identical to other gene transcripts to avoid non-specific gene silencing.

Using the methods described herein, RNA preparations that are specific for a single member of a gene family and do not silence mRNA from other members of that gene family can be prepared from long dsRNA that is complementary in sequence to a segment of the target mRNA (also referred to as long dsRNA segments). Alternatively, RNA preparations can be prepared that have specificity for any gene in a gene family but do not have specificity for other genes outside the gene family.

The appropriate gene silencing effect may be achieved by targeting mRNA sequences that are unique or that form part or all of a consensus region for a family of mRNAs.

An assay which may be readily used to determine whether a mutant RNase III has improved cleavage activity compared to other enzyme preparations includes an in vivo and an in vitro test as follows:

(1) In vivo assay: dsRNA having a sequence complementary to a transcript of a marker protein is subjected to RNase III digestion to produce a heterogeneous dsRNA fragment preparation. Host cells normally expressing the marker protein are transfected with the RNA fragment preparation and changes in the expression of the marker phenotype determined to ascertain whether a knock down effect in gene expression has occurred as a result of the transfection with the RNA fragment mixture. The in vivo assay has been described in more detail in US published application US-2004-0038278 incorporated herein by reference.

(2) In vitro assay: dsRNA is subjected to RNase III digestion and the digest run on acrylamide gels to determine the size of fragments produced at various times of incubation and in selected buffers.

The methods described herein can also be applied to producing multiple dsRNA fragment mixtures which can then be used to simultaneously silence multiple genes. Additional uses include targeting upstream or downstream regulatory regions with dsRNA to modulate expression. Accordingly, a heterogeneous population of large dsRNA fragments obtained from transcription of a single DNA template or a plurality of different DNA templates can be digested by mutant RNase III in the presence of magnesium ions.

The above described generation of dsRNA fragment mixtures or clones thereof for making selected siRNA fragments can be achieved in part or as a whole by utilizing a kit of the type described in Example V. Instructions can be provided that include any or all of descriptions of how to make a desired large dsRNA, to generate dsRNA mixtures and to transfect cells with such mixtures.

Illustrative Uses

The availability of hsiRNA fragments provides a supply of a reagent or therapeutic agent and a novel therapeutic approach in which a desired knockdown effect can be achieved in a whole organism without the disadvantages of gene therapy. However, clones expressing siRNA fragments or dsRNA mixtures can be used for complete, modulated or transient in vivo silencing of a target gene.

A gene derived from a pathogen can be targeted for inhibition. For example, the gene could cause immunosuppression of the host directly or be essential for replication of the pathogen, transmission of the pathogen or maintenance of the infection. The inhibitory RNA could be introduced in cells in vitro or ex vivo and then subsequently placed into an organism to effect therapy, or the organism could be directly treated by in vivo administration. A method of gene therapy can be envisioned. For example, cells at risk for infection by a pathogen or already infected cells, particularly human immunodeficiency virus (HIV) infections, may be targeted for treatment by introduction of RNA according to the invention. The target gene might be a pathogen or host gene responsible for entry of a pathogen into its host, drug metabolism by the pathogen or host, replication or integration of the pathogen's genome, establishment or spread of an infection in the host, or assembly of the next generation of pathogen. Methods of prophylaxis (i.e., prevention or decreased risk of infection), as well as reduction in the frequency or severity of symptoms associated with infection, can be envisioned.

Embodiments of the present invention may be applied to treatment or development of treatments for cancers of any type, including solid tumors and leukemias.

Embodiments of the present invention are exemplified as follows. These Examples are provided to aid in the understanding of the invention and are not construed as a limitation thereof.

All references cited herein are incorporated by reference, including U.S. provisional applications 60/538,805, 60/572,240 and 60/543,880.

EXAMPLES

Example I

Preparation of E. coli RNAse III Mutants

All E. coli RNAse III mutants (except for E117D which was generated by mutagenesis using PCR were constructed by a standard 2 step PCR sewing technique (Methods Enzymol. 185: 60-89 (1990)). Other cloning techniques used herein are standard in the art and can be found in Sambrook, J., Fritsch, E. F., Maniatis, T. "Molecular Cloning: A Laboratory Manual", Cold Spring Harbor Laboratory Press, Cold Spring Harbor, N.Y., 1989. The starting plasmid was E. coli RNAse III cloned into pET16B (EMD Bioscience, Inc., San Diego, Calif.), which produced a His-tagged RNAse III protein under control of a T7 promoter.

WT RNAse III

E. coli RNAse III was amplified from a pMalE/RNAse III clone with the following primers:

```
ACAGGATCCCATGAACCCCATCGTAATTAAT    (SEQ ID NO:1)

ACAGGATCCTCTAGAGTCATTCCAGCTCCAGTTTTT  (SEQ ID NO:2)
```

The PCR product was cleaved with BamHI and cloned into the BamHI site of pET16b, resulting in a plasmid that synthesizes His-tagged WT RNAse III. This His-tagged WT RNAse III clone in pET16b was used as a substrate in PCR reactions to create all amino acid substitution mutations (except for E117D) as described below.

Formation of E38A Mutant

The primers used to construct the carboxy terminal half of E.coli RNase III (Accession No. X02946) with an E38A mutation were:

```
CAGTAAACATAACGCGCGTTTAGAAT         (SEQ ID NO:3)

ACAGGATCCTCTAGAGTCATTCCAGCTCCAGTTTTT  (SEQ ID NO:2)
```

The primers used to construct the amino terminal half of RNAse III with an E38A mutation were:

```
    AATTCTAAACGCGCGTTATGTTTACT       (SEQ ID NO:4)

TAATACGACTCACTATAGGG (SEQ ID
    NO:7)
    (NEB primer cat#1248 (New England Biolabs,
    Inc., Beverly, MA).
```

The two PCR products were then 'sewn' together in one PCR reaction using both as substrates and primers (SEQ ID NOS:7 and 2) for the reaction. The resulting product was then cleaved with Xba I and cloned back into a modified pET16b at an XbaI site, resulting in a His-tagged RNAse III with an E38A mutation.

Formation of E65A RNase III

E65A RNAse III was constructed in a similar two-step process. In the first step, the His-tagged RNAse III plasmid was amplified with the following primer sets in two PCR's:

```
CTCGTGTGGATGCAGGCGATATGAGCCGGAT        (SEQ ID NO:5)

ACAGGATCCTCTAGAGTCATTCCAGCTCCAGTTTTT   (SEQ ID NO:2)
to amply the 3' end of the gene.

TCCGGCTCATATCGCCTGCATCCACACGAGGGA      (SEQ ID NO:6)

TAATACGACTCACTATAGGG                   (SEQ ID NO:7)
(NEB primer cat#1248 (New England Biolabs, Inc.,
Beverly, MA) to amplify the 5' end of the gene.
```

The two PCR products were then used as substrates in a subsequent PCR reaction and cloned into the XbaI site of the modified pET16b vector described in I.B.

Formation of Additional RNAse III Mutants

Any specific point mutation can be constructed from the cloned wt RNAse III gene by a similar method to the one described to create both the E38A and E65A mutants. In the first step, two primers, one for the coding strand and one for the non-coding strands, are designed such that they introduce the desired mutation at the selected amino acid. The primers are of sufficient length and span such that they would still anneal to the substrate given the mismatch necessary to introduce the mutation. The primer for the coding strand is matched with an appropriate downstream primer on the opposite strand in PCR that amplifies this region of the RNAse III gene. A similar PCR is performed using the non-coding primer and an appropriate primer upstream on the opposite strand that results in an overlapping upstream fragment of the RNAse III gene. The two fragments are 'sewn' together using the two fragments as substrates and the outside primers. The resulting RNAse III gene now contains the point mutation desired and can be cloned back into the appropriate vector. All mutations with the exception of E117D were constructed in this way.

The E38 residue of the E. coli RNAse III gene corresponds to the E37 residue of the Aquifex aeolicus RNAse III gene. Likewise D45 corresponds to D44, E65 corresponds to E64, E117 to E110. This was determined by several standard multiple sequence alignment software packages. The corresponding amino acid residues can be determined for any RNAse III gene by similar methods.

Example II

Production and Purification of RNase III Mutants

Expression & Purification 30 ml cultures of each mutant and WT clones were grown in E. coli ER2566 (New England Biolabs, Inc., Beverly, Mass.) to mid log phase, then induced by the addition of IPTG to a final concentration of 100 μM and shaken at 15° C. overnight. Induced cultures were lysed by sonication.

The RNase III mutants were purified from the cleared lysates by Qiagen Nickel resin affinity purification (according to manufacturer's instructions) and assayed by standard methods. The enzyme reaction was performed in NEB Buffer 2 (New England Biolabs, Inc., Beverly, Mass.), at 37° C., for 1 hr using 0.5 μg of a 900 bp dsRNA as a substrate. The product of the reaction was analyzed by non-denaturing polyacrylamide electrophoresis.

RNase Activity Assay 0.5 μg of MalE dsRNA (HiScribe kit-NEB, New England Biolabs, Inc., Beverly, Mass.) was digested with RNAse III (wt and mutants in the range consistent with optimal conditions in a 20 μl reaction mixture at 37° C. in NEB Buffer 2 (0.05 M NaCl, 50 mM Tris-HCl, pH 7.9, 10 mM $MgCl_2$, 1 mM dithiothreitol) (New England Biolabs, Inc., Beverly, Mass.) for 1 hour.

As can be seen in the FIG. 3A, the end product of digestion of dsRNA with E38A is predominantly a dsRNA fragment of about 23 bps in length (lanes 7, 8, and 9). This product appears in as little as 1 minute and the reaction is 'complete' by 10 minutes (FIG. 6). In addition the 23 bp product is stable for at least 16 hrs (FIG. 3B, lanes 7-9) and is slowly lost over several days (FIG. 5).

The activity of E65A (FIG. 10) is in direct contrast to what was reported in (Blaszczyk, J., et al. *Structure* 9:1225-1236 (2001)). In this paper the authors describe an E65A mutation of RNase III as disabling RNAse III function. By our assay, E65A produced a similar product to E38A (FIG. 10, lanes 6-8). However, the product appears to be less stable and has disappeared by 16 hrs (FIG. 10B, Lanes 4 & 6).

Example III dsRNA cleavage and Gene Silencing Activity in Cultured Cells.

To test the ability of the dsRNA product of RNase III mutant digestion to induce RNA interference, an in vivo assay according to US published application US-2004-0038278 was carried as follows: dsRNA made from firefly luciferase encoding DNA sequence was cleaved with the wt RNAseIII (Shortcut) or E38A mutant RNase IIIs (FIG. 9 ). NIH 3T3 cells were transfected with a reporter plasmid expressing the firefly luciferase gene, another reporter acting as a transfection control and dsRNA. Cells transfected with the reporters and no dsRNA or unrelated digested dsRNA show significant luciferase activity. The cells transfected with hsiRNA from wild type or mutant Rnase III show a knockdown of luciferase activity. The results are shown in FIG. 9.

Example IV

The cleavage products of E38A RNase III on dsRNA is a set of heterogeneous fragments that are overlapping.

Short dsRNA cleavage products of mutant RNase III digestion contain sequences representing the entire parent sequence. This is determined by cloning and sequencing the dsRNA cleavage products or by hybridization to the template DNA sequence fragments. Generation of a library of cloned RNase III products is readily achieved. The techniques used here to demonstrate the presence of overlapping fragments are the same as those described in US published application US-2004-0038278 herein incorporated by reference.

Example V

Kits for Generating hsiRNA and for Gene Silencing in Mammalian Cells

A kit is provided for in vitro generation of dsRNA mixtures and optionally for transfection of RNA fragments into mammalian cells.

In an embodiment of the invention, each kit contains reagents for processing multiple large dsRNAs for transfection of cells and includes instructions for use.

Kit Components

The kit may contain enzyme and optionally vectors, primers and/or buffers. The kit may include one or more of the reagents listed below (each obtainable from New England Biolabs (Beverly, Mass.)).

| | |
|---|---|
| T7 RNA Polymerase, 150 units/μl, | 25 μl |
| 10X Buffer/NTPs (see formulation below) | 60 μl |
| 30X High Molecular Weight Component Mix (HMW) (see formulation below) | 20 μl |
| BT7-minimal Primer (19 MER), 5'-Biotin-dCTCGAGTAATACGACTCACTATAGG-3', (SEQ ID NO: 26) (10 μM) | 25 μL |
| 10X Mutant Ribonuclease III (1.4 μg/μl) | 100 μL |
| 10X hsiRNA Buffer (see formulation below) | |
| 10X EDTA (250 mM) | 1000 μL |
| Litmus 38iluc control template, | 1 μg |
| RNase-free glycogen 10 μg/μL | 50 μL |

Plasmid DNA 500 μg/ml in TE buffer (10 mM Tris-HCl, pH 8.0, 1 mM EDTA)

In addition, the kit may include transfection reagents, RNA size markers and Streptavidin-coated beads.

Buffer Compositions
(a) 10× Buffer/NTPs:
  400 mM Tris-HCl, pH 8.1
  190 mM $MgCl_2$
  50 mM DTT
  10 mM spermidine
  40 mM each NTP
(b) 30× High Molecular Weight (HMW) Mix:
  20 mM Tris-HCl, pH 8.1
  1.5 mg/ml BSA
  100 units/ml inorganic pyrophosphatase (yeast)
  12,000 units/ml pancreatic ribonuclease inhibitor
  50% glycerol
(c) 10× hsiRNA buffer
  0.5M Tris-HCl, pH 7.5
  0.5M NaCl
  0.1M $MgCl_2$
  110 mM DTT The kit utilizes mutant RNase III in an optimized buffer to produce fragments in the range of about 18-30 nt (more particularly 21-23 nt) from long dsRNA. The dsRNA product is cleaved with mutant RNase III to reproducibly yield dsRNA mixtures suitable for silencing gene expression. The sequences of different siRNA fragments in the mixture map to sequences along the entire target gene. The dsRNA mixtures can be purified by ethanol precipitation and used in transfection.

An example of instructions accompanying the kit include the following:

(1) Cloning the DNA template prior to in vitro transcription to generate dsRNA

One approach to making a DNA template for transcription is to clone a DNA of interest in Litmus 28i/38i bidirectional transcription vectors (New England Biolabs, Inc., Beverly, Mass.). The DNA of interest can then be amplified by PCR using a single T7 promoter-specific primer such as a BT7 Minimal Primer which produces a linear product with the target sequence flanked by T7 promoters which define the ends.

Alternatively target gene-specific primers with appended T7 promoters can be used to amplify any specific CDNA sequences. For example, the amplification primer:

```
5'TAATACGACTCACTATAGaaggacagatggttaagtac-3'
   T7 promoter               (SEQ ID NO:8)
``` in which a T7 promoter (underlined) located at the 5' end preceding the target-specific sequence (bold) can be used for amplifying any cDNA template.

Biotinylated BT7 primer can be used to amplify any sequence flanked by T7 promoters. Optionally, the amplified biotinylated DNA template can be isolated by binding to streptavidin magnetic beads (New England Biolabs, Inc., Beverly, Mass.) and used directly as a template for transcription. For forming an immobilized DNA template, 25-50 µL of streptavidin magnetic bead suspension is added to the amplification (PCR) reaction mix with an equal volume of 1 M NaCl and incubate at room temperature for 10-15 minutes. The supernatant is removed in the presence of a magnet and the beads washed with 0.5 mLs TE, 0.5 M NaCl. The resuspended beads can be used directly in the transcription reaction. In vitro transcription of the immobilized DNA template produces DNA-free dsRNA.

Amplification can be achieved by any polymerase dependent method such as PCR. The amplification product is purified by ethanol precipitation, or by a chromatographic method (e.g., QiaQuick® column (Qiagen, Studio City, Calif.)) and resuspended in TE (10 mM Tris-HCl, pH 8.0, 1 mM EDTA, prepared with Milli-Q water or equivalent) to a final concentration of ~500 µg/ml.

A control consisting of GL3 luciferase can be prepared using a Litmus 38iLuc plasmid in which a 1.0-kbp fragment of the GL3 luciferase gene is cloned in the SphI and NgoMIV sites of Litmus 38i. Linearization with MfeI and StuI (in separate reactions), followed by in vitro transcription of the combined linearized templates, produces dsRNA 1.0 kbp in length.

Pilot studies can be undertaken for providing an hsiRNA mixture for specific gene silencing using one or more fragments obtained by cleaving dsRNA having a length of 100-600 bp including RNA derived from restriction fragments of a cDNA which has been subcloned into Litmus28i/38i vectors (New England Biolabs, Inc., Beverly, Mass.).

In vitro Transcription

In vitro transcription is performed using the DNA template prepared as described above. The volume of template used in the transcription reaction depends on the method of purification. For unpurified PCR product, no more than 5 µl is used per 30 µl reaction. The amount of added template DNA should not exceed 1 µg per 30 µl reaction.

| RNase-Free Water | 50 – x µl |
|---|---|
| 10X Buffer/NTPs | 6 µl |
| DNA template (~0.5-1 µg) | x µl |
| 30X HMW Mix | 2 µl |
| T7 RNA Polymerase (150 U/µl) | 2 µl |
| | 60 µl |

Incubation at 42° C. can improve yields of RNA transcripts containing substantial secondary structure. As it is difficult to gauge the secondary structure content in a particular transcript, we recommend that all transcription be carried out at 42° C. if possible. Transcription yields increase linearly for the first 90 minutes (approximately) and reach maximum after 2-3 hours. Reactions can be carried out overnight if desired, but yields will not be higher. Double-stranded RNA is stable upon prolonged incubation at 37° C.

The transcription reaction can be analyzed on a 1% agarose gel taking care to avoid RNase contamination. Double-stranded RNA migrates approximately as the DNA template used in the reaction. The expected length of the transcript from the Litmus 38iluc control template is 1000 bp.

The dsRNA transcription product is purified by ethanol precipitation. One-tenth volume of 3 M NaOAc is added at a pH 5.5 with 2 volumes of cold 95% ethanol. Incubate on ice for 15 minutes, or store at −20° C. overnight. Spin for 15 minutes in a microcentrifuge at 14,000 rpm. Remove supernatant, add two volumes 80% ethanol, incubate at room temperature for 10 minutes, centrifuge for 5 minutes, and decant and drain the tube. Allow the pellet to air-dry. Dissolve the dried RNA in 10 mM Tris-HCl, pH 8.0, 1 mM EDTA, or dH$_2$O.

Forming an dsRNA Mixture

Use 1× (10-fold diluted) RNase III at a concentration of (0.14 µg/ul) and 0.07 µg/pL of dsRNA in the digestion reaction as in the following example.

Combine the following:

| dH$_2$O | 120 – x µL |
|---|---|
| 10X hsiRNA Buffer | 15 µl |
| dsRNA | x µL (10 µg) |
| mutant RNaseIII | 15 µl |
| | 150 µl |

Incubate for 10 min at 37° C.

Promptly add 15 µl 10× EDTA to stop the reaction.

For monitoring the products of digestion, a 10-20% native polyacrylamide gel is suitable. The product of digestion reveals that the long dsRNA has been cleaved to yield an dsRNA mixture of fragments having a size in the range of 18-25 nucleotides regardless of the length of the starting long dsRNA. The mixture can be purified by the single step of ethanol precipitation prior to use in transfection.

Ethanol Precipitation of hsiRNA Fragments

Add one-tenth volume of 3 M NaOAc, pH 5.5, 2 µL glycogen solution and 3 volumes of cold 95% ethanol. Place at −70° C. for 30 minutes, or −20° C. for 2 hrs-overnight. Spin for 15 minutes in a microcentrifuge at 14,000 rpm. Remove supernatant carefully avoiding the small pellet, add two volumes 80% ethanol, incubate at room temperature for 10 minutes, centrifuge for 5 minutes, and decant and drain the tube. Allow the pellet to air-dry. Dissolve the dried RNA in 10 mM Tris-HCl, pH 8.0, 1 mM EDTA, or dH$_2$O.

Determining dsRNA Concentration

This can be measured using a UV spectrophotometer (OD at 260 nm of 1 corresponds to 40 µg/mL dsRNA) or a fluorometer (using RIBOGREEN®, Molecular Probes, Eugene, Oreg.) or comparisons to siRNA standards used in the art.

Transfection Guidelines

After ethanol precipitation, dsRNA mixtures can be directly transfected into mammalian cells using reagents and protocols suitable for oligonucleotide transfections such as lipofectin 2000, oligofectamine, TRANS-IT TKO® (Mirus Corp., Madison, Wis.) and Targefect (Targeting Systems, Santee, Calif.) or trnasfection reagents provided by New England Biolabs Inc. (Beverly. Mass.). Additionally, Calcium Phosphate and Electroporation have been reported to be efficient in transfecting short RNAs.

Amounts of 25-100 ng of dsRNA can be used per transfection well (24-well format) as an initial amount to be adjusted according to experimental findings.

Large dsRNA may be synthesized by in vitro transcription as described above using a modified transcription buffer containing modified ribonucleotides in place of NTPS in 10× bufffer described above such as 2-fluoro-ribo-CTP, 2-fluoro-ribo-UTP, 2-O-methyl-ribo-CTP, 2-O-methyl-ribo-UTP, 2-O-methyl-ribo-ATP, 2-O-methyl-ribo-GTP or other 2' modifications that render the dsRNA more stable or resistant to degradation. A DURASCRIBE® kit (Epicentre Technologies, Madison, Wis.) may be used for these purposes.

Example VI

Specific siRNA Mixtures

Segments of mRNA sequence for an identified target can be selected subsequent to a sequence comparison with the gene database conducted with each target sequence.

An algorithm is used to scan the sequence using a window of, for example, 16-21 bp. BLAST scores can then be obtained for each segment after alignment with a complete database (such as UNIGENE). Those entries calculated from the BLAST scores that are higher than a set limit were eliminated from the report. Regions of the target sequence showing absence of hits to other targets are preferably selected.

Although there is no particular limitation on segment size, segments may be selected in the range of about 150-1000 bp for example, 200-400 bp long.

A selected DNA segment corresponding to target dsRNA can be amplified using PCR primers that amplify efficiently using standard protocols for PCR primer design. For example, primers may include a T7 promoter sequence at the 5' end. Other sequences can be used in place of the T7 promoter to facilitate cloning to one of the double T7 promoter vectors (Litmus 28i, Litmus 38i, Litmus-U from New England Biolabs, Inc., Beverly, Mass.).

For Litmus U, the following primer sequences can be used: gggaaagu and ggagacau, where u stands for uracil. After the PCR reaction, the amplified DNA product can be cloned directly in Litmus U using the USER protocol (New England Biolabs, Inc., Beverly, Mass.). The cloned fragments may then be used for the production of dsRNA (see for example US published application US-2004-0038278).

Each sequence determined to be suitable for use in preparing hsiRNA is described by accession number and sequence in Table 1.

Preparation of hsiRNA mixtures is described in Example II.

The functionality of the hsiRNA mixtures can be determined by transfecting cells as described in Example III. In addition, Western blot or protein activity assays can be performed at time points after transfection to determine whether gene expression has been down regulated.

TABLE 1

| CATEGORY | TARGET | Acc. number | Coordinates |
|---|---|---|---|
| kinases | Akt1 | NM_005163 | 199-657 |
|  | Erk2 | NM_002745 | 660-940 |
|  | MSK1 | AF074393 | 282-736 |
|  | p38 | L35253 | 10-419 |
|  | IRS1 | NM005544 | 1026-1713 |

TABLE 1-continued

| CATEGORY | TARGET | Acc. number | Coordinates |
|---|---|---|---|
|  | PKR | M35663 | 999-1499 |
|  | PTEN | NM_000314 | 1019-1445 |
| transcription | CREB | M34356 | 247-601 |
| Nuc. signaling | ERa | NM_000125 | 369-905 |
|  | ERb | NM_001437 | 587-1240 |
|  | DAX | NM_000475 | 1-249 |
|  | p53 | NM_000546 | 717-915 |
|  | DNMT1 | X69632-G-BPR2 | 2124-3235 |
|  | DnMT3B | AF331857 | 1150-1545 |
|  | DnMT3A | X63692.gb-pr2 | 1547-2388 |
|  | TRIP | L38810 | 1-445 |
|  | Rb | m15400.gb_pr1 | 2239-2755 |
|  | MeCP2 | af030876.gb_pr | 699-1011 |
| Other | caspase3 | p42574 | 1063-1496 |
|  | La | NM_003142 | 316-631 |
|  | FURIN | NM002569 | 1781-1990 |
| Controls, | Lit28i polylinker | NEB#N3528S | 2465-2600 |
| gen. use | EGFP | U55763 | 596-1322 |
|  | RFP | AF272711 | 152-632 |
|  | FfLUC | U47295 | 747-1757 |
|  | *Renilla* | AF264722 | 3673-3951 |

Table 1 lists examples of target genes for which hsiRNA fragments can be prepared using mutant RNaseIII as described herein and used for gene silencing in cells that are cultured or occur in vivo. The coordinates for the gene (cDNA) sequence are contained in accession number of GenBank given above.

Algorithm for selection of suitable RNA sequences for forming an hsiRNA mixture.

1. The target sequence SO of length N is input from the user.
2. All possible oligonucleotide subsequences ($S_1$, $S_2$, $S_3$ . . . $S_{(n-L+1)}$) of a user-specified length L are extracted from SO.
3. The nucleotide composition of each oligonucleotide subsequence is calculated.
4. The thermal stability or free energy of helix formation is calculated along each oligonucleotide subsequence. For purposes of this calculation, the sequence is treated as a double stranded RNA duplex with 2 base 3' overhangs.
5. (optional) The differential stability of the 2 ends of the double stranded RNA duplex is calculated. Differentials where the stability of the 5' sense strand end are marked as favorable. The opposite differential is marked unfavorable.
6. A database of sequences representing the transcriptome of the user-selected target organism is queried with sequence SO to identify sequences with a user-specified level of similarity to SO. These similar sequences are marked as equivalent to the target sequence and their identities are recorded.
7. The same transcriptome database of the user-selected target organism is queried to determine the frequency of occurrence of each oligonucleotide subsequence within the transcriptome. An occurrence of the oligonucleotide subsequence is recorded if the oligonucleotide subsequence has a user-specified level of similarity to a subsequence from the transcriptome database. For each occurrence, the identity of the matching segments within the transcriptome is recorded as well. These matching segments are termed "cross target" or "off target" matches. Sequences identified as equivalent to the target SO in the preceding step are filtered out and not counted as cross target matches.
8. For each oligonucleotide subsequence, data representing the frequency of of cross-target matches in the transcriptome, the nucleotide composition and the differential thermal stability of its ends are presented.

9. Generally, regions with low cross-target frequencies, moderate % GC composition and high density of favorable differential thermal stability are considered desirable regions for subsequent primer selection.

In the current embodiment of this algorithm, the megablast program from NCBI which uses a variant of the BLAST algorithm is used to search the transcriptome database. The similarity measure used to identify cross-targets is the presence of a user-specified minimum number of contiguous nucleotide matches between the target oligonucleotide subsequence and the subject sequence in the transcriptome database. The nucleotide composition measure displayed is % GC. Thermal stability at the ends of the oligonucleotide subsequence is calculated using the 4 terminal base paired nucleotides and excludes the unpaired overhanging sequence.

What is claimed is:

1. A method, comprising:

reacting a preparation of large double-stranded RNA (dsRNA) with an effective amount of a mutant RNAseIII in a magnesium- or manganese-containing buffer to produce a heterogeneous mixture of fragments in which at least 15% of the fragments have a size of 18-25 nucleotides, wherein the at least 15% of the fragments are not substantially degraded in the presence of the effective amount of the mutant RNaseIII for at least 1 hour, the heterogeneous mixture comprising heterogeneous short interfering double-stranded RNA (hsiRNA) suitable for silencing gene expression, the mutation comprising E38A, in *E. coil* RNaseIII.

2. A method, comprising:

forming a heterogeneous mixture of fragments by incubating a large double-stranded RNA (dsRNA) with a mutant RNaseIII for an effective time for cleaving, in the presence of magnesium ions or manganese ions, at least 90% of the large dsRNA is cleaved, where cleavage can be detected by gel electrophoresis and ethidium bromide staining wherein at least 30% of the cleaved dsRNA has a fragment size of 18-30 nt, the mutation in the RNase III comprising E38A.

* * * * *

UNITED STATES PATENT AND TRADEMARK OFFICE
CERTIFICATE OF CORRECTION

PATENT NO. : 7,695,964 B2
APPLICATION NO. : 10/586720
DATED : April 13, 2010
INVENTOR(S) : Sanjay Kumar et al.

Page 1 of 1

It is certified that error appears in the above-identified patent and that said Letters Patent is hereby corrected as shown below:

At column 7, line number 39, before "(PROSITE:" insert -- (SEQ ID NO:27) --, thereat.

At column 15, line number 9, delete "$_1$" and insert -- 1 --, therefor.

At column 16, line number 46, delete "110" and insert -- 10 --, therefor.

At column 17, line number 2, delete "CDNA" and insert -- cDNA --, therefor.

At column 18, line number 22, delete "µg/pL" and insert -- µg/µL --, therefor.

Signed and Sealed this

Seventeenth Day of May, 2011

David J. Kappos
*Director of the United States Patent and Trademark Office*